(12) United States Patent
Shachaf

(10) Patent No.: US 9,903,806 B2
(45) Date of Patent: Feb. 27, 2018

(54) FOCUSING SYSTEM WITH FILTER FOR OPEN OR CLOSED LOOP CONTROL

(71) Applicant: Nanometrics Incorporated, Milpitas, CA (US)

(72) Inventor: Amit Shachaf, Los Gatos, CA (US)

(73) Assignee: Nanometrics Incorporated, Milpitas, CA (US)

( * ) Notice: Subject to any disclaimer, the term of this patent is extended or adjusted under 35 U.S.C. 154(b) by 415 days.

(21) Appl. No.: 14/109,564

(22) Filed: Dec. 17, 2013

(65) Prior Publication Data

US 2015/0168290 A1   Jun. 18, 2015

(51) Int. Cl.
 *G01J 4/00* (2006.01)
 *G01N 21/21* (2006.01)
 *G02B 7/28* (2006.01)

(52) U.S. Cl.
 CPC ............. *G01N 21/211* (2013.01); *G02B 7/28* (2013.01)

(58) Field of Classification Search
 CPC ........... G01N 21/211; G01N 2021/213; G01B 11/0641; G02B 7/28; G02B 7/285
 See application file for complete search history.

(56) References Cited

U.S. PATENT DOCUMENTS

| | | | |
|---|---|---|---|
| 5,486,701 A | | 1/1996 | Norton et al. |
| 5,596,411 A | * | 1/1997 | Fanton et al. ................. 356/369 |
| 5,608,526 A | | 3/1997 | Piwonka-Corle et al. |
| 5,995,143 A | | 11/1999 | Price et al. |
| 6,791,684 B2 | * | 9/2004 | Ferrieu ................. G01N 21/211 250/225 |
| 6,970,789 B2 | * | 11/2005 | Ippolito et al. ................. 702/21 |
| 7,295,307 B2 | * | 11/2007 | Naka .................... G01N 21/211 356/301 |

(Continued)

FOREIGN PATENT DOCUMENTS

| | | |
|---|---|---|
| EP | 0031483 B1 | 7/1981 |
| WO | WO 2012/138541 A1 | 10/2012 |

OTHER PUBLICATIONS

International Search Report and Written Opinion dated Jun. 10, 2015 for International Application No. PCT/US2014/066707 filed on Nov. 20, 2014 by Nanometrics Incorporated, 17 pages.

(Continued)

*Primary Examiner* — Kara E Geisel
*Assistant Examiner* — Rufus Phillips
(74) *Attorney, Agent, or Firm* — Silicon Valley Patent Group LLP

(57) ABSTRACT

An optical metrology device, such as an ellipsometer, includes a focusing system that adjusts the focal position of the metrology device in real time so that focus may be maintained during movement of the measurement locations on the sample, e.g., using closed loop control. A filtered focus signal may be used to adjust the focal position while moving to a measurement location. Additionally, the focus signal may be coarsely filtered and finely filtered, where a coarse filtered focus signal is used to adjust the focal position while moving to a measurement location and a fine filtered focus signal is used to adjust the focal position when at the measurement location. An open loop control may be used in which once at the measurement location, a filtered focus signal is used to adjust the focal position when the filtered focus signal has no offset with respect to the focus signal.

36 Claims, 10 Drawing Sheets

(56) References Cited

U.S. PATENT DOCUMENTS

| | | | |
|---|---|---|---|
| 7,719,677 B2* | 5/2010 | Rosengaus | G01J 3/02 |
| | | | 356/300 |
| 7,724,375 B1 | 5/2010 | Novikov et al. | |
| 8,559,008 B2* | 10/2013 | Blasenheim | G02B 7/28 |
| | | | 356/364 |
| 8,767,209 B2* | 7/2014 | Li | G01J 3/02 |
| | | | 356/369 |
| 2003/0071190 A1 | 4/2003 | Chen et al. | |
| 2006/0017676 A1 | 1/2006 | Bowers et al. | |
| 2014/0098369 A1* | 4/2014 | Blasenheim | G02B 7/28 |
| | | | 356/369 |

OTHER PUBLICATIONS

Invitation to Pay Additional Fees dated Feb. 25, 2015 for International Application No. PCT/US2014/066707 filed on Nov. 20, 2014 by Nanometrics Incorporated, 5 pages.

* cited by examiner

FOCUSING SYSTEM WITH FILTER FOR OPEN OR CLOSED LOOP CONTROL

BACKGROUND

Ellipsometers are optical metrology devices that detect changes in the polarization state of light reflected from a surface of a sample in order to measure characteristics of the sample. By way of example, FIG. 1 illustrates a conventional spectroscopic ellipsometer 10 that includes a broad band light source 12, a polarizer 14 and lens 15 to focus the illuminating light on the surface of a sample 16 that is positioned on a stage 18. The ellipsometer 10 further includes an analyzer 22 after passing through lens 20. After passing through analyzer 22, the reflected light is focused by lens system 24 on a detector 26.

The ellipsometer 10 must be properly focused on the sample. Some systems use independent focusing systems, i.e., systems that attached to the ellipsometer, but that use an independent light path to determine the position of the focusing system, and thus, the ellipsometer, with respect to the sample. Such focusing systems, however, require very precise alignment, which is expensive and difficult. FIG. 1 illustrates example of an integrated focusing system that includes a mirror 28 with an aperture 30. The mirror 28 reflects the outside rays of the reflected beam to a focus detector 32, while the inner rays of the reflected beam are transmitted through the aperture 30 and received by the ellipsometer detector 26. Typically, the focus detector 32 is a position sensitive device (PSD) or a "quad cell", neither of which image the detected light but, in principle, sums all of the light that is received. Accordingly, such devices are susceptible to inaccuracies due to stray light. Other systems, such as that described in U.S. Pat. No. 5,608,526, use a camera as the focus detector 32. Nevertheless, such a system still suffers from imprecision due to systematic errors caused by the mirror 28, because only the outer part of the beam is sampled by detector 32. Moreover, a focus system, such as that described in U.S. Pat. No. 5,608,526, lack the precision required to produce a small illuminating spot size on the sample.

Accordingly, an improved focusing system for ellipsometers is desired.

SUMMARY

An optical metrology device, such as an ellipsometer, includes a focusing system that adjusts the focal position of the metrology device in real time so that focus may be maintained during movement of the measurement locations on the sample, e.g., using closed loop control. A filtered focus signal may be used to adjust the focal position while moving to a measurement location. Additionally, the focus signal may be coarsely filtered and finely filtered, where a coarse filtered focus signal is used to adjust the focal position while moving to a measurement location and a fine filtered focus signal is used to adjust the focal position when at the measurement location. An open loop control may be used in which once at the measurement location, a filtered focus signal is used to adjust the focal position when the filtered focus signal has no offset with respect to the focus signal.

In one implementation, a method of focusing an ellipsometer includes generating radiation; polarizing the radiation to produce a sample beam that is incident on and reflected by a sample to produce reflected radiation; producing relative lateral movement between the sample and optics of the ellipsometer to position the optics at a desired measurement location with respect to the sample; determining a deviation from a desired focal position for the ellipsometer relative to the sample using a portion of the reflected radiation and generating a focus signal; and adjusting a focal position of the ellipsometer based on the focus signal to focus the sample beam on the sample while producing the relative lateral movement between the sample and the optics of the ellipsometer.

In one implementation, a method of focusing an optical metrology device includes generating radiation that is incident on and reflected from a sample to produce reflected radiation; producing relative lateral movement between the sample and optics of the optical metrology device to position the optics at a desired measurement location with respect to the sample; detecting a focus signal using at least a portion of the reflected radiation; applying a filter to the focus signal to produce a filtered focus signal; adjusting a focal position of the optical metrology device based on the filtered focus signal while producing the relative lateral movement between the sample and the optics of the optical metrology device.

In one implementation, a method of focusing an optical metrology device includes generating radiation that is incident on and reflected from a sample to produce reflected radiation; detecting a focus signal using at least a portion of the reflected radiation; applying a first filter to the focus signal to produce a first filtered focus signal; adjusting a focal position of the optical metrology device with respect to the sample using the first filtered focus signal; determining when a mean amplitude displacement between the first filtered focus signal and the focus signal is within a threshold range; applying a second filter to the focus signal to produce a second filtered focus signal when the mean amplitude displacement between the first filtered focus signal and the focus signal is within the threshold range, wherein the second filter reduces amplitude of noise in the focus signal more than the first filter; and adjusting the focal position of the optical metrology device using the second filtered focus signal to focus the radiation on the sample.

DETAILED DESCRIPTION

Figure 2:
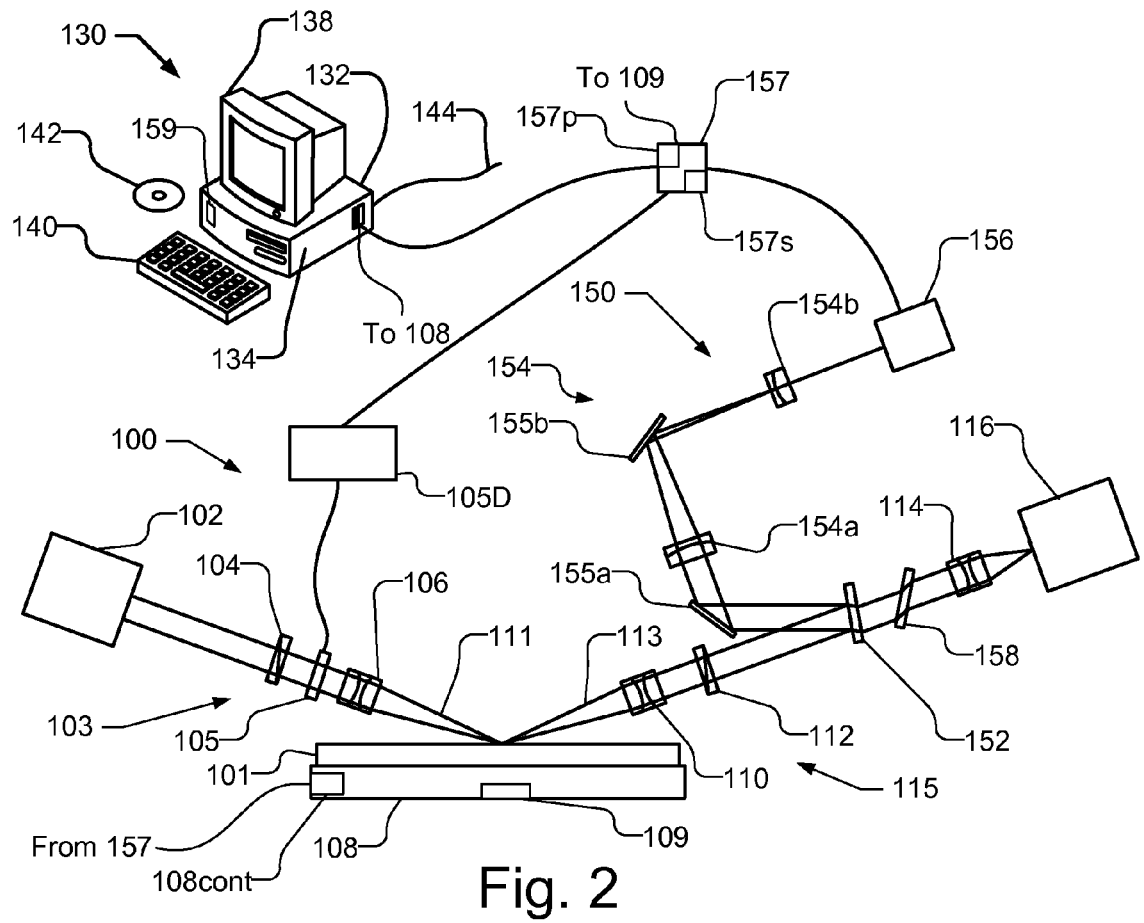
FIG. 2 illustrates an ellipsometer 100 with a high precision focusing system in accordance with an embodiment of the present invention.

FIG. 2 illustrates an ellipsometer 100 with a high precision focusing system 150. Ellipsometer 100 is illustrated as including a light source 102 and a polarization state generator 103 with a polarizer 104 and a rotating compensator 105, as well as a lens system 106, which focuses the illuminating light 111 on the surface of a sample 101 that is positioned on a stage 108. Ellipsometer 100 may be monochromatic or spectroscopic. The incident illuminating light 111 has a known polarization state due to the polarizer 104 and rotating compensator. The polarization state of the light reflected by the sample 101 is analyzed by a polarization state analyzer 115, e.g., by passing the reflected light 113 through another polarizer 112, commonly referred to as analyzer 112, after passing through another lens system 110. After passing through the analyzer 112, the reflected light 113 is focused by a lens system 114 on a detector 116.

The ellipsometer 100 includes an integrated auto focusing system 150 that images the same light rays that are used by the ellipsometer 100 and additionally magnifies the deviation from a best focus position. Focusing system 150 includes a beam splitter 152 that directs a portion of the reflected light 113 to a lens system 154 that may include fold mirrors 155a, 155b if desired. The lens system 154 focuses the light onto a camera 156.

Figure 3:
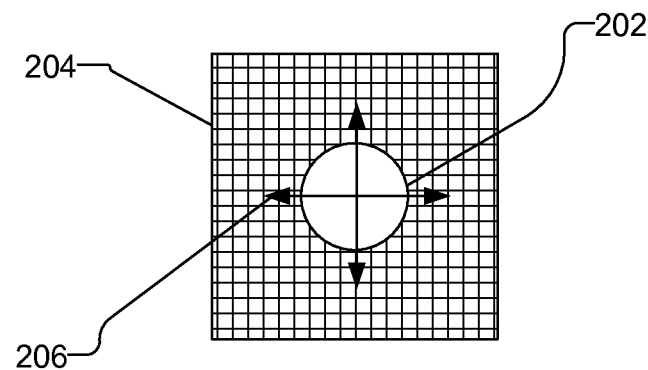
FIG. 3 illustrates a two-dimensional sensor of a camera in the focusing system with a significantly smaller light spot thereon.

As illustrated in FIG. 3, the lens system 154 focus the light into a spot 202 that is significantly smaller than the sensor 204 for the camera 156. The sensor 204 may be, e.g., a two dimensional sensor array such as a CCD. The spot 202 may be 1%-50%, e.g., 10% or less, of the size of the sensor 204, which increases the useful auto-focus range. The lenses of lens system 154, illustrated by lenses 154a and 154b in FIG. 2, are arranged to magnify the deviation from the best focus position thereby providing greater measurement precision. For example, as illustrated by arrow 206 in FIG. 3, the movement of the location of the spot 202 on the sensor 204 provides a magnified indication of the deviation from the best focus position. The size of the spot on the sensor 204 may change slightly as the sample 101 is scanned through the focal range, however, this is a relatively small effect to which the spot location calculation may be configured to be insensitive. The magnification produced by lens system 154 with respect to the deviation from the best focus position may be 2× to 5× or greater, such as 10×. However, reduction of spot size decreases the focus precision and, thus, a trade-off between auto focus range and precision is made, as smaller spot makes the spot location calculation less precise but provides a higher spot intensity. Accordingly, if desired, a large spot, e.g., the size of the sensor 204 may be produced, which may be used to provide a more accurate spot location calculation.

As illustrated in FIG. 2, the beam splitter 152 of the focusing system 150 reflects a portion of the reflected light 113, e.g., 4% to 10% of the total light intensity, to the focusing system 150, and transmits the remaining portion of the reflected light 113, e.g., 90% or more of the total light intensity, to the ellipsometer detector 116. In the configuration illustrated in FIG. 2, the reflected portion is provided to the focusing system 150, but if desired, the transmitted portion of the reflected light 113 may be provided to the focusing system 150, where 4% to 10% of the reflected light intensity is transmitted. The use of beam splitter 152, which is sometimes referred to as a "pick off" beam splitter, is advantageous as the entire cross section of the reflected light 113 beam is sampled by the focusing system 150, as opposed to the system shown in FIG. 1, in which only the outside rays of the reflected light are used. By sampling the entire beam of the reflected light 113, the focusing system 150 is insensitive to systematic errors caused by sampling only portions of the reflected light 113.

The beam splitter 152 will produce some optical aberrations in the reflected light 113. Accordingly, if the aberrations from beam splitter 152 are too high, a compensator 158 may be used between the beam splitter 152 and the detector 116. The compensator 158 is configured to correct, e.g., eliminate or reduce, the aberrations caused by the beam splitter 152. With the use of an appropriately configured compensator 158, optical aberrations in the ellipsometer 100 may be very low, thereby enabling the measurement of the sample 101 using a small spot size, e.g., less than 100 µm.

As illustrated in FIG. 2, the camera 156 for the focus system 150 is coupled to a computer 130, e.g., through a frame grabber board 157. The rotating compensator 105 and stage 108 may also be connected to the frame grabber board 157 directly or through controller/drivers (105D). If desired, the detector 116 for the ellipsometer 100 may be coupled to the same computer 130 or a different computer. The computer 130 includes a processor 132 with memory 134, as well as a user interface including e.g., a display 138 and input devices 140. The frame grabber board 157 includes a processor 157p, (which may be a field programmable gate array (FPGA)) that is configured to determine a focus error, which is used to control the focus position of the stage 108, e.g., via a stage servo controller 108cont that receives focus error data from the frame grabber board 157 and controls an actuator 109 in the stage 108 accordingly. Thus, in one embodiment, the frame grabber board 157 is processing the focus error directly from the camera 156 and providing the focus adjustment to the stage servo controller 108cont without input from the computer 130. Of course, if desired, computer 130 may be used in part or all of the processing of the focus error and instructing the stage servo controller 108cont. It should be understood that a processor, such as processor 157p on frame grabber board 157, may include one or more separate processing units, e.g., processor 157p may include a first processor for image processing and a separate processor for focus error determination. Additionally, one or more processors may be located in other positions, besides frame grabber board 157. For example, processor 157p (or one or more of the processor units that comprise processor 157p) may be located in camera 156, or elsewhere.

If the processor 157p is, e.g., a microprocessor, that carries out instructions of a computer program, the data structures and software code for automatically implementing one or more acts described in this detailed description can be implemented by one of ordinary skill in the art in light of the present disclosure and stored, e.g., on a computer readable storage medium 157s, which may be any device or medium that can store code and/or data for use by a computer system. The computer-usable storage medium 157s may be, but is not limited to, magnetic and optical storage devices such as disk drives, magnetic tape, compact discs, and DVDs (digital versatile discs or digital video discs). A communication port may also be used to receive instructions that are used to program the processor 157p to perform any one or more of the functions described herein and may represent any type of communication connection, such as to the internet or any other computer network. Additionally, the functions described herein may be embodied in whole or in part within the circuitry of an application specific integrated circuit (ASIC) or a programmable logic device (PLD), and the functions may be embodied in a computer understandable descriptor language which may be used to create an ASIC or PLD that operates as herein described. For example, as discussed above, a field programmable gate array (FPGA) may be used. The FPGA may be either in the camera 156 or on a frame grabber board 157 internal or external to the computer 130. Where processor 157p is an FPGA, computer readable storage medium 157s may provide the programming file to embed the desired configuration in the processor 157p, which may be performed one time for a non-volatile FPGA, or otherwise at power-up. By avoiding the use of the main system CPU to perform the necessary calculations for auto focusing, the CPU is not slowed down. Further, a dedicated processor increases the image processing speed. Thus, the stage servo controller 108cont may be directly coupled to the frame grabber board 157, which may provide a signal directly to the stage servo controller 108cont through a Serial Peripheral communication Interface (SPI) channel.

Most digital cameras, such as those used in conventional metrology systems include an internal auto exposure control. The auto exposure control of such cameras, however, is inadequate for the present high precision focusing system 150, which uses a single spot on the CCD. Auto exposure control in conventional cameras attempts to adjust the exposure for the whole CCD and thus will lose control when there is single spot on the CCD. Moreover, if the image is downloaded to the computer 130 to perform the exposure control, there would be too much delay, which would lead to unstable control. Thus, the focusing system 150 uses the camera exposure control I/O as a slave to the image processing dedicated processor, e.g., on the camera 156 or frame grabber board 157, so the exposure control is in good correlation to what is needed in the image processing. The exposure is adjusted with respect to only the spot on the CCD and not the entire CCD, which is, e.g., 99% empty. Thus, once the spot is located on the sensor 204, the exposure error based on the local intensity of the spot is calculated, as opposed to calculating the exposure error over the entire sensor. The exposure control I/O is set based on the exposure error calculation for the spot and is provided to a proportional-integral-derivative controller (PID) controller 159 in the frame grabber board 157 to predict the exposure time and/or gain for the camera 156 to create a stable exposure for the spot that follows the, e.g., 40 Hz sinusoidal, changes in the spot intensity.

Typically auto exposure algorithms require the acquisition of several images at several different exposure/gain settings to accurately calculate the correct exposure time/gain for the camera. As discussed above, however, the signal intensity is constantly changing as the rotating optic rotates, so the exposure time/gain would be constantly changing. Consequently, in a conventional system, the exposure time/gain for each desired exposure would have to be recalculated requiring the acquisition of several images at several different exposure time/gain settings to accurately calculate the correct exposure time/gain for each exposure. It is desirable to sample the auto focus signal as frequently as possible, and thus acquiring several images for each exposure would reduce the speed of the system. The PID controller 159, however, can calculate the next exposure time can be calculated to sufficient accuracy in real time so that the additional images are not necessary. The PID controller 159 may sample at about 40 times per cycle, enough to make a PID loop effective. The PID controller 159 may be on the FPGA processor 157p in the frame grabber board 157, which is performing the image processing, and thus, it may perform at full speed and sample every image if desired.

As is known in the art, an ellipsometer, such as ellipsometer 100, used to measure the properties and/or structures of a thin sample on a substrate vary the polarization state of the light going to the sample. There are a few standard ways of doing this, all of which are contemplated with the present disclosure. One way to vary the polarization state is to continuously rotate the polarizer 104 about the optical axis, while the analyzer 112, which transmits only one polarization state, is fixed. In this method, there is no need for rotating compensator 105. In the simplest case, where the sample does not change the polarization of the incident light, the result is a variation in the intensity of the light after the analyzer 112. For example, the analyzer 112 could be set to transmit only horizontally polarized light, and block vertically polarized light. With the polarizer 104 starting in a position in which the illuminating light 111 is horizontally polarized, the analyzer 112 would transmit 100% of the light. As the polarizer 104 rotates 90 degrees about the optical axis, the light is now vertically polarized. As a result, the analyzer 112 will block all of the light, and there will be no signal at the detector 116. As the polarizer moves another 90 degrees (180 degrees total) it is now transmitting horizontally polarized light again, and the analyzer would again transmit 100% of the light. A plot of the signal intensity vs. time, thus, produces a sine wave, where the intensity of the signal varies between 0% and 100% and the frequency of the sine wave is double the frequency of the rotation of the polarizer 104. Additionally, the analyzer 112 may rotate, while the polarizer 104 is held fixed. Alternatively, a rotating compensator 105, as illustrated in FIG. 2, may be used to vary the polarization state. The rotating compensator 105 will produce the same basic sinusoidal variation of intensity vs. time. Further, the rotating compensator 105 may be located on either side of the sample 101.

In use, a sample under test will change the polarization state of the incident light, which will change the intensity and phase of the resulting signal from the detector 116. Using the change in intensity and phase, the material properties of the sample 101 may be determined, which is the essence of ellipsometry and is well known in the art. However, changes in the intensity and phase also produce problems in an auto focus system for ellipsometers. When the intensity of the signal getting through the analyzer 112 drops to near zero, the auto focus camera 156 does not receive enough light to measure a spot location. This, in turn, creates problems with the auto focus system 150, because the servo control signal has vanished. Thus, the auto focus system 150 is configured to compensate for the periodic loss of an actuator control signal using filtering and interpolation to compensate for missing signal points.

The rotating compensator 105 (or polarizer 104) produces another problem for the auto focus system 150. In the ideal case, as the rotating optic (i.e., the compensator 105 or polarizer 104) rotates, the location of the illumination spot on the sample 101 does not move. However, the motor and bearings that rotate the rotating optic are not perfect, resulting in a wobble of the rotating optic. In addition, the input beam to the rotating optic and the output beam after the rotating optic will not be perfectly parallel. As a result of these two effects, the illumination spot on the sample 101 does move, which causes the spot to move on the two-dimensional sensor as the rotating optic rotates. The movement of the illumination spot in ellipsometer 100 is typically less than 2 µm, which despite being a small amount, is sufficient to cause problems for the auto focus system 150. Accordingly, the auto focus system 150 is configured to compensate for the movement of the illumination spot.

Additionally, some samples will scatter unwanted light into the path of the auto focus system 150. The amount and pattern of unwanted light will vary depending on the sample. While the optical system of the ellipsometer 100 may be designed to minimize receiving scattered light, the problem cannot be completely eliminated. If the unwanted or scattered light is not excluded from the spot location calculations of the auto focus system, errors will be produced. Accordingly, the auto focus system 150 is configured to be insensitive to scattered light.

Figure 4:
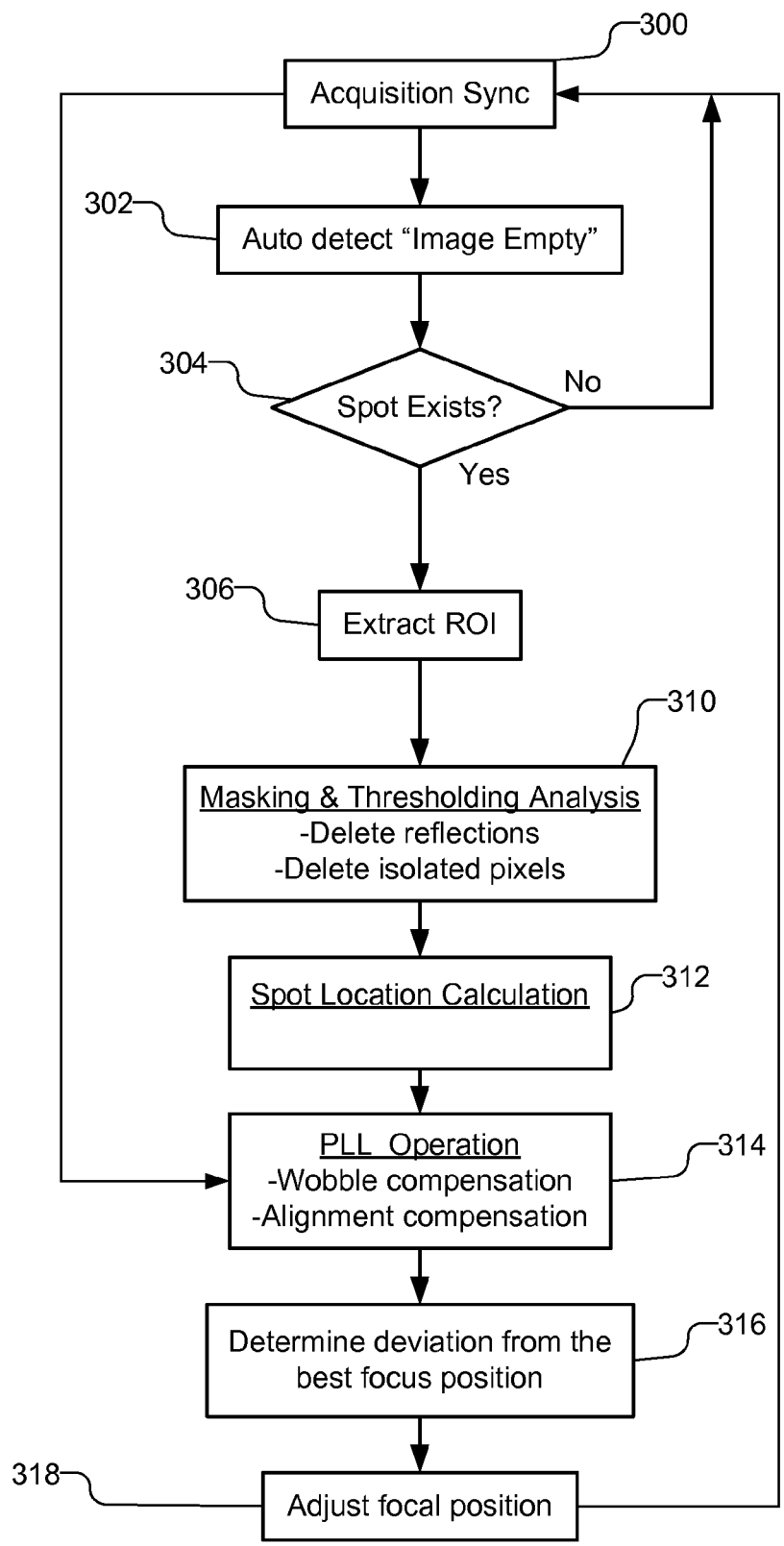
FIG. 4 is a flow chart illustrating processing of the sensor signal provided by the camera to automatically adjust the focal position of the ellipsometer.

FIG. 4 illustrates a flow chart of the auto focus process, which may be performed completely or in part by camera 156 or frame grabber board 157, e.g., (FPGA and DSP), external to the computer 130. As illustrated, an acquisition synchronization 300 step is performed, in which the controller/driver 105D for the rotating compensator 105 (or polarizer 104) provides a synchronization (trigger) signal to the frame grabber board 157 to be used to compensate for spot movement on the sample, as discussed below. An auto detection of an empty image is performed (302). An empty image is detected, e.g., by finding a threshold level to separate the spot from the background by auto thresholding, which well known in the art of image processing. If a spot does not exist (304), i.e., there is no ROI, and the process starts over with acquisition synchronization 300. If a spot does exist (304), the region of interest may be extracted from the image (306). If desired, e.g., where the spot size is as large as the sensor 204 or where the processor is sufficiently powerful, such as when an FPGA is used in the frame grabber board 157, a ROI is not extracted and the whole image is calculated directly.

To extract the ROI (306), the image is summed horizontally (X) and vertically (Y) into vectors and the maximum in both vectors is found in X and Y. Using the maximum in X and Y, the ROI can be located and extracted in the image data. The spot can then be determined from the 2D data of the image in the ROI. Masking and thresholding is then performed (310) to filter noise from the signal. In this step, a histogram showing the number of pixels at a given intensity is produced. Most of the pixels receive little or no signal, so there will be a large peak near zero intensity. The pixels that are illuminated in the auto focus spot will produce a second peak. However, some pixels outside the auto focus spot may be illuminated due to background or scattered light, which are to be removed. To determine if any given pixel is part of the auto focus spot or part of the background, a technique, such as inter class variation auto threshold algorithm, may be employed. The pixels that are part of the auto focus spot are retained, while pixels that are determined to be outside the auto focus spot, e.g., due to reflections or isolated pixels are eliminated or masked.

The spot location calculation for the pixels inside the mask is then performed (312). In one embodiment, the spot location may be determined based on the centroid of the spot. Other techniques, however, may be used to calculate the spot location. For example, the average x, y location of the pixels in the spot may be used to determine a location of a center of the spot, or a smoothing function may be used to smooth the points in the spot and the maximum may be used as the location of the center of the spot. Alternatively, the center of the spot may be found using a large scale optimization problem, e.g., by treating the perimeter of the spot as an ellipse and finding the center of the ellipse. Of course, other techniques or variation of the above may be used if desired. By way of example, the location of the spot may be calculated as a centroid based on the gray level values (or, alternatively, the binary values) of pixels that have an intensity that is greater than the threshold. A simple centroid calculation would be to assume that all of the pixels inside of the mask are weighted equally, i.e., binary centroid calculation. However, it has been found that when the spot has a Gaussian distribution, the brighter pixels near the center of the "blob" of remaining pixels have less noise than the dimmer pixels at the edge of the blob. Accordingly, a grey level centroid may be produced using a centroid calculation that is weighted by the pixel intensity (aka grey scale), where brighter pixels have a stronger weighting in the calculation according to their intensity, which improves the focus precision. The use of a binary centroid calculation, however, may be advantageous when the internal structure of the spot is not homogenous and is changing in correlation to the changes on the wafer patterns. The auto focus system should be insensitive to the wafer pattern so in that case a binary centroid calculation may be used.

A phase locked loop (PLL) operation may be used (314) to synchronize with the angular position of the rotating optics, so that wobble in the rotating optics may be compensated. As discussed above, the controller/driver 105D for the rotating optic (i.e., compensator 105 or polarizer 104) outputs a signal indicating the angular position of the rotating optic, which is acquired during the acquisition synchronization (300) step. Using the angular position signal as a "trigger" signal, a PLL is used to lock on the trigger signal and compensation for any wobble in the rotating optic may be performed using a look up table (LUT) in the FPGA in the camera 156 or frame grabber board 157 (or in computer 130), where the values of the look up table are obtained through a calibration procedure. The system may be calibrated, e.g., using a silicon wafer, where the rotating optic is rotated one or more rotations. The average spot location shift for every trigger angle is determined and loaded into the LUT. Those values will be subtracted from the calculated position base on the current angular position of the rotating optic. Because the wobble is hardware dependent, i.e., a property of the optical components of the ellipsometer, and does not change with alignment, this calibration is not expected to change frequently.

Additionally, with the PLL locked on the synchronization signal from the rotating optics, a LUT may be used (314) to compensate for alignment. The location of the spot on the sensor is calculated based on pixels units and not in nanometer units. The center of the sensor 204, however, might not be perfectly aligned to perfect focus for the ellipsometer. Moreover, motion of the spot on the sensor 204 may not be linear, for example, because the motion of the spot on the sensor 204 is the result of angular motion, while the sensor 204 is linear. Thus, a second LUT may be loaded into memory based on automatic calibration procedure to compensate for linearity, to shift the zero position, and to translate pixels into nanometers. In other words, the alignment LUT is obtained by stepping through the Z axis and comparing the ellipsometer best focus to the spot location on CCD in pixels, which is analyzed and loaded into a LUT so that a spot location in pixels may be input to the LUT and the focus errors in microns or stage encoder counts is output from the LUT.

Figure 5:
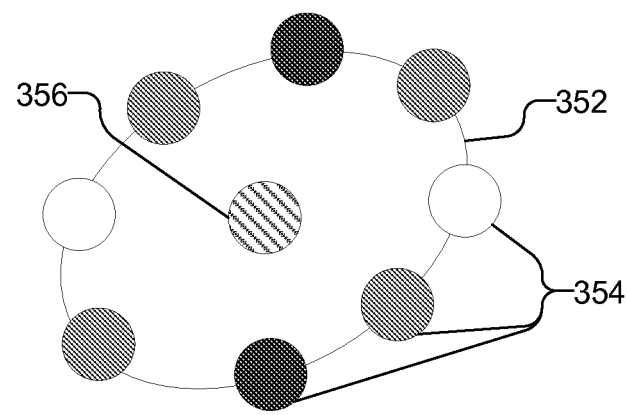
FIG. 5 illustrates movement of the auto focus spot on the sensor due to the wobble of rotating optics.

FIG. 5 illustrates movement of the auto focus spot on the sensor 204 due to the wobble of the rotating optics and the correction of the movement to produce a centered auto focus spot described in step 314. The outer ellipse 352 represents the movement of the illumination spot, where the spots 354 represents a sequence of eight exposures as the rotating optic rotates 360°. The spot location is calculated for every image frame individually and thus, in practice, there are more than eight exposures for 360° rotation of the optics. The different gray levels of the spots 354 represent different intensities. As the rotating optic, e.g., compensator 105, rotates, the focus spot location on the auto focus sensor 204 follows the path of an ellipse, even though the focus has not changed. Thus, the image acquisition is synchronized with the angular position of the rotating optic. The rotating optic hardware may be designed to send, e.g., 13 trigger signals per 360° rotation of the rotating optics. The use of the PLL, as discussed above, permits division the ellipse 352 into any desired number of angles. During calibration, an XY position fix on the sensor 204 is obtained for every desired angular position of the rotating optic. The position fix is stored in the compensation LUT. Spot 356 in FIG. 5 represents the corrected location produced using the PLL operation (314), which is the location of the auto focus spot if the rotating optics had no wobble.

For example, during calibration, the ellipsometer 100 is placed above a blank silicon wafer in that is in focus. The PLL will lock on the triggering signal from the compensator signal and produce camera triggers at the predefined acquisition angles. The camera 156 will capture images at every designated angle (triggering from the PLL logic). By way of example, in FIG. 5, eight acquisition angles are shown, but additional (or fewer) acquisition angles may be used, e.g., 13 angles. The XY offset from the center of the sensor is calculated for each image. The offset is stored in the LUT. At run time, the PLL will subtract the XY offset that corresponds with the current acquisition angle stored in the LUT from the calculated spot location. The acquisition angles are constant and repeatable and handled by the PLL logic. Because the ellipsometer hardware, i.e., the rotating optic, may have a fixed division of angles, e.g., 13, which may not be equally distributed, the PLL may be synchronized to only the first trigger from the rotating optic in every rotation. The PLL may then generate its own triggers for itself and the camera 156 for the desired division of the acquisition angles.

The deviation from a best focus position is then determined based on deviation of the corrected spot (316) to the center of the sensor 204. The focal position of the ellipsometer 100 is adjusted accordingly (318), e.g., by sending the results to a servo controller for the actuator 109 to move the stage 108.

The focusing system may be used to focus the metrology device on the sample in real time, thereby reducing focus time as well as enabling closed loop control over the servo-controller. Accordingly, if desired, the metrology device may maintain focus on the sample while the sample and/or optical head is moved, effectively following the topography of the sample while moving to a new measurement location. As focus has been maintained while moving to a new measurement location, upon arrival at the new measurement location very little or no adjustment to the focal position is required, thereby improving throughput.

Figure 6:
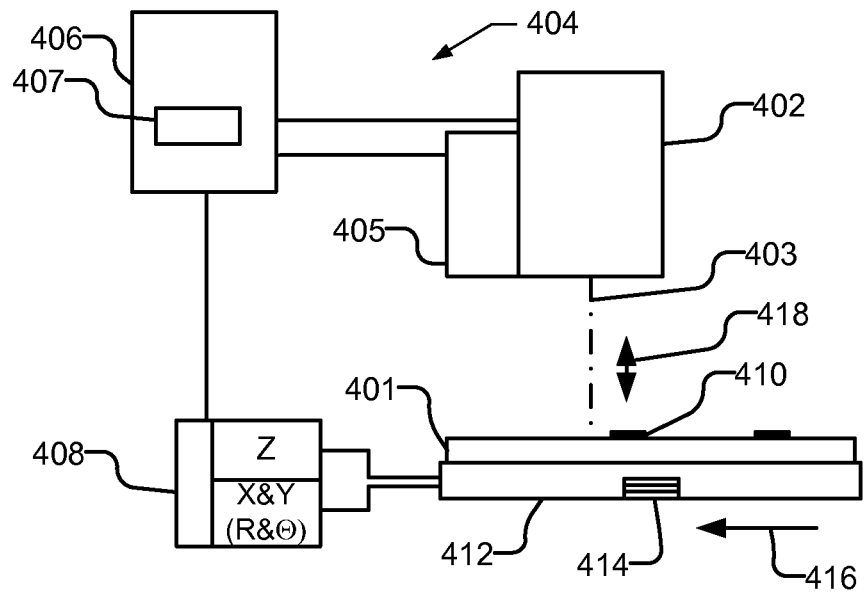
FIG. 6 is a block diagram illustrating an optical metrology device with a focusing system, which may be used in a closed loop control to maintain focus of the optical metrology device during movement.

FIG. 6, by way of example, is a block diagram illustrating an optical metrology device 402 with a focusing system 404 that is used to control the focal position of the optical metrology device 402 on the sample 401, e.g., during lateral movement to measurement locations 410. The focusing system 404 and the optical metrology device 402 may be the same as the focusing system and ellipsometer, respectively, discussed above. If desired, however, other types of optical metrology devices, such as a reflectometer, scatterometer, etc., may be used in place of the focusing ellipsometer. If optical metrology devices, other than an ellipsometer, is used, the focusing system 404 may vary from the focusing system discussed above, as appropriate. If desired, the focusing system 404 may use a portion of the reflected sample beam generated by the optical metrology device 402, to generate a focus signal. Alternatively, focusing system 404 may use light that is separate from the light used by the optical metrology device 402.

FIG. 6 illustrates focusing system 404 as including an optical system 405 coupled to the optical metrology device 402 and the processing system 406, referred to herein as computer 406, coupled to receives signals from the optical system 405 and determine a deviation from a desired focal position. The computer 406 may also be coupled to the optical metrology device 402 to control and receive measurement data from the optical metrology device 402. The computer 406 may be the same as computer 130 discussed above. Moreover, if desired, different aspects of processing the signals from optical system 405 to determine a deviation from the desired focal position and/or generating control signals to adjust the focal position of the optical metrology device 402 may occur in separate or the sample processing components. For example, as discussed above, a frame grabber board 157 may be disposed between the optical system 405 and the computer 406. The computer 406 receives and analyzes the signals from the optical system 405 and provides the servo controller 408 with focus signals. One or more filters 407 may be used to filter the raw focus signal to smooth the signal, thereby reducing noise, while preserving edges in the signal, which may be caused, e.g., when there is lateral movement between the sample 401 and the optical metrology device 402. For example, the filter 407 may be a non-linear, edge-preserving and noise-reducing smoothing filter. The filter 407 may filter both in domain, i.e., closeness of the pixels or signals, and in the range, i.e., similarity of the pixels or signals, such as performed by a bilateral filter. Accordingly, filter 407 is sometimes referred to herein as a bilateral filter 407. In one implementation, the bilateral filter 407 may use a Kalman filter, or other similar type of predictive filter that runs in real-time, instead of a Gaussian filter, which is commonly used in bilateral filters.

A servo controller 408 controls the lateral motion between the stage 412 and the optical metrology device 402, e.g., in the X and Y directions (or R and Θ) directions via actuators 414, which for the sake of simplicity are illustrated as controlling only the stage 412. It should be understood that horizontal motion between stage 412 and optical metrology device 402 may be produced by movement of either or both the stage 412 and optical metrology device 402. The servo controller 408 also controls the vertical motion between the stage 412 and the optical metrology device 402 (with optical system 405), e.g., in the Z direction via actuators 414, to adjust the focal position of the optical metrology device 402. Again, it should be understood that vertical motion between stage 412 and optical metrology device 402 may be produced by movement of either or both the stage 412 and optical metrology device 402.

As illustrated in FIG. 6, the servo-controller 408 may cause actuator 414 to produce relative lateral (horizontal) movement (illustrated by arrow 416) between the sample 401 and the optical metrology device 402, or more specifically, optics within the optical metrology device 402 to position the optics at a desired measurement location 410 with respect to the sample 401. The position of the optics of the optical metrology device 402 is illustrated in FIG. 6 by sample beam 403. The focusing system 404 determines a deviation from a desired focal position, e.g., as discussed above. The raw focus signal is filtered to smooth the signal which may then be provided to the servo-controller 408 and the servo-controller 408 adjusts the focal position of the optical metrology device (as illustrated by arrow 418) to focus the sample beam 403 on the sample. Additionally, the filter preserves edges in the signal, thereby allowing real-time detection of large changes in the raw focus signal, e.g., caused during lateral movement between the sample 401 and the optical metrology device 402. Moreover, the filter 407 may produce use relatively coarse or fine settings to produce relatively coarse focusing and fine focusing, which may be applied at different times based on whether there is lateral movement as well as the quality of the focus. Consequently, the servo-controller 408 may adjust the focal position of the optical metrology device (as illustrated by arrow 418) in real-time, e.g., using coarse focusing, while there is relative lateral movement 416 between the sample 401 and the optics of the optical metrology device 402 and may adjust the focal position using relatively fine focusing after lateral movement stops. Once the focus position of the optical metrology device 402 is at the desired focal position using the relatively fine focusing, the focusing system 404 may provide an in-focus signal to prevent the servo-controller 408 from producing any further vertical motion between the optical metrology device 402 and the sample 401, thereby preventing jitter during the optical metrology of the sample 401.

Figure 7:
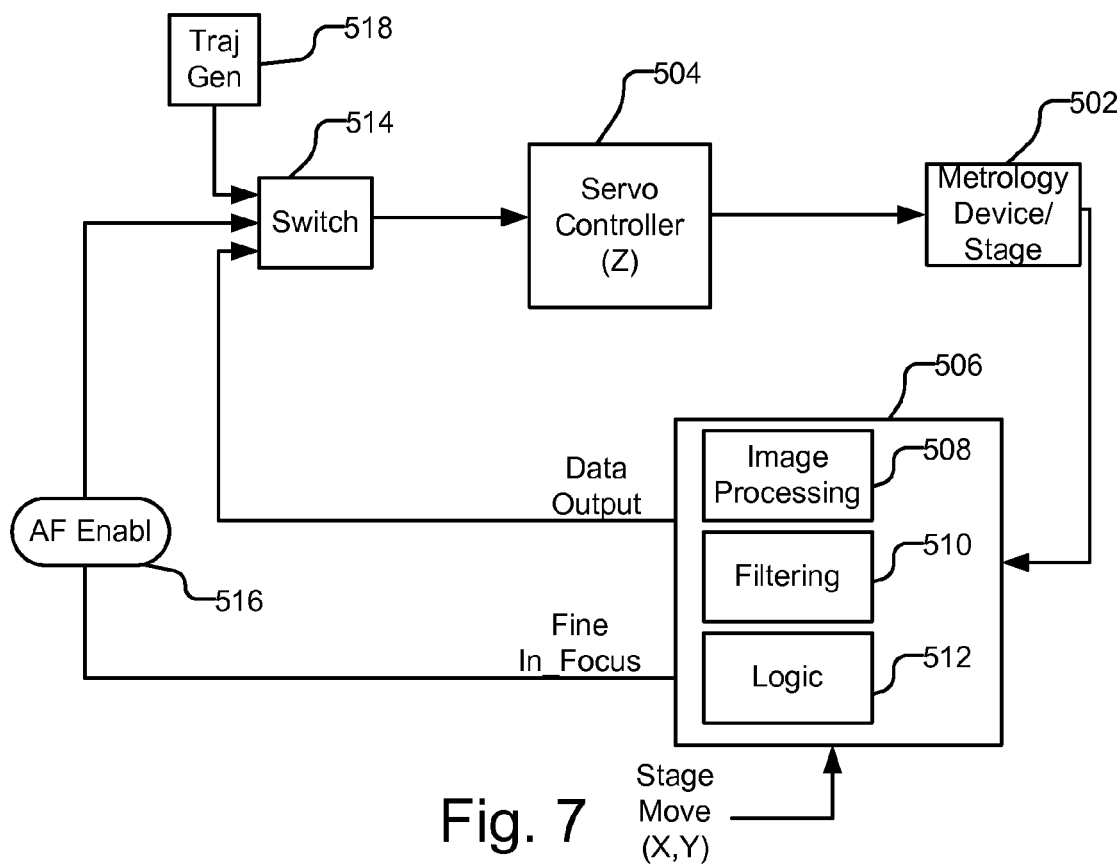
FIG. 7 is a block diagram illustrating the closed loop control of a focusing system.

FIG. 7 is a block diagram illustrating an autofocus system of a metrology device 502 including closed loop control. The focal position of the metrology device 502 is controlled by a servo controller 504 that controls the vertical position (Z) between the optical system of the metrology device 502 and a sample under test. A focus system 506 is coupled to receive a raw focus signal from focusing optics in the metrology device 502. The focus system 506 may also receive a Stage Move signal which indicates lateral (X, Y) movement between the metrology device 502 and a sample. The focus system 506 may include image processing 508, filtering 510 and in focus logic 512 to analyze the raw focus signal and to provide a control signal as the data output and a Fine In_Focus signal. The image processing 508 may be, e.g., based on spot location determination as discussed above, and filtering and in focus logic 512 is discussed below. The control signal is provided to the servo controller 504, e.g., via switch 514, and the servo controller 504 adjusts the vertical position (Z) between the optical system of the metrology device 502 and the sample under test appropriately. The Fine In_Focus signal may be provided to an autofocus enable block 516 is coupled to switch 514 to enable autofocus when the Fine In_Focus signal indicates that the metrology device is not at the proper focal position, and disable autofocus when the Fine In_Focus signal indicates that the metrology device is at the proper focal position. The autofocus system may include additional components, such as a trajectory generator 518 to provide an initial trajectory to the servo controller 504 to place the metrology device at a desired focal position. Additional components that are not necessary for understanding the present invention may be included, but are not illustrated in FIG. 7, such as serial peripheral interface (SPI) communication between the focus system 506 and the servo controller 504, filtering and amplification of the servo controller signals, proportional-integral-derivative (PID) processing of control signals, etc.

Figure 8:
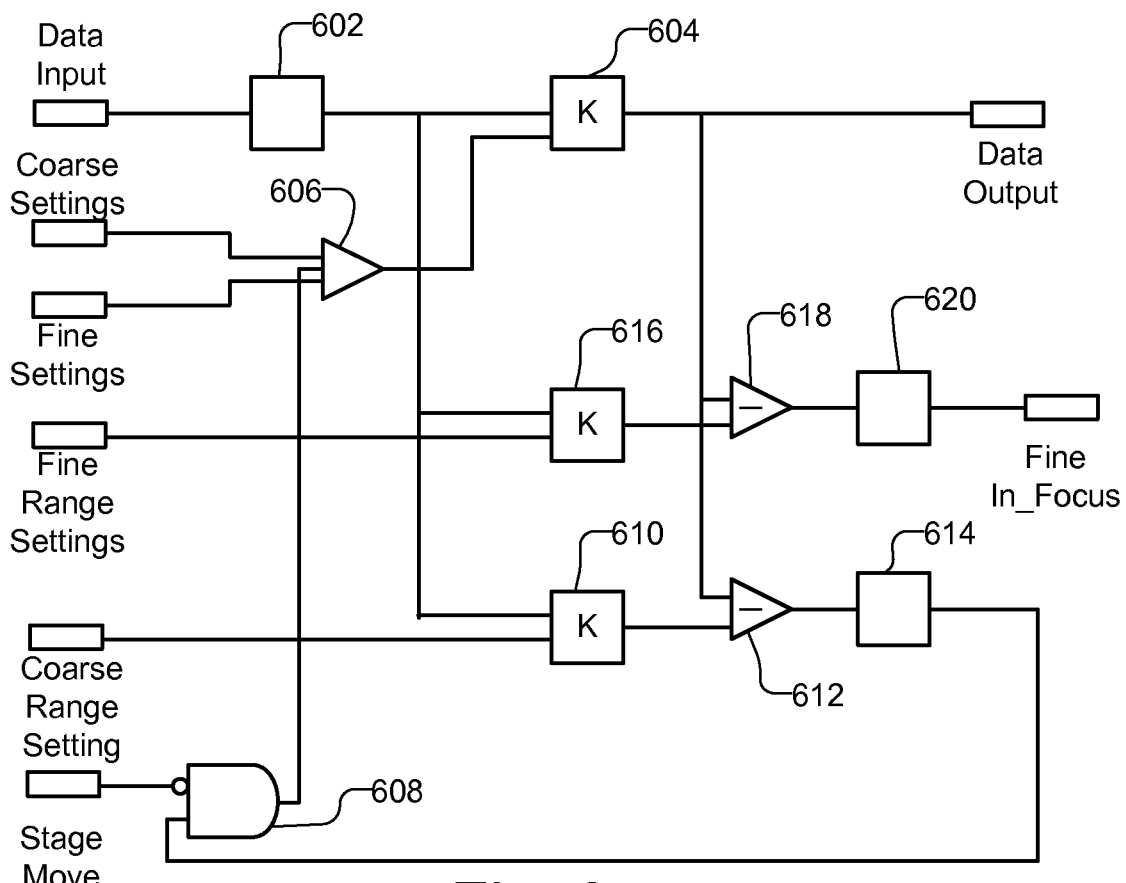
FIG. 8 is a schematic illustrating filtering of the focusing signals from the focus system.

FIG. 8 is a schematic illustration of a bilateral filter and logic that may be used for filtering 510 in focus logic 512 in the focus system 506 of FIG. 7. The raw focus signal, e.g., from image processing 508, is received at the input terminal Data Input. The raw focus signal may be provided to a filter 602 to remove outliers in the raw focus signal. The raw focus signal is provided to a filter 604 that reduces the noise in the focus signal while preserving edges in the signal, and provides the resulting filtered focus signal to the output terminal Data Output. By way of example, the filter 604 may be a Kalman filter or other similar type of predictive filter that runs in real-time. The filter 604 may receive via switch 606 relatively coarse filter settings and relatively fine filter settings, which may be provided via respective terminals Course Settings and Fine Settings. The fine filter settings cause the filter 604 to reduce the amplitude of the noise in the raw focus signal by an amount that is greater than the coarse filter settings. The coarse filter settings, however, preserver greater edge detail in the received raw focus signal than the fine filter settings. It should be understood that filter 604 uses coarse filter settings or fine filter settings and, thus, functions as two separate filters, i.e., filter 604 may be considered a first filter when applying the coarse filter settings and a second filter when applying the fine filter settings. If desired, filter 604 may be replaced with two separate filters enabled, e.g., by a switch similar to switch 606, with one filter applying the course filter settings and the other filter applying the fine filter settings.

Switch 606 may be controlled by logic gate 608 to provide the course filter settings or fine filter settings based on whether there is lateral movement between the metrology device and the sample, e.g., to align the optics of the optical metrology device with a desired measurement location (as provided by the signal at terminal Stage Move). By way of example, the coarse filter settings may be used when the sample and/or optical metrology device is moving laterally, so that during lateral movement, a coarse filtered focus signal is provided at terminal Data Output and is used to adjust the focal position of the optical metrology device. Accordingly, the optical metrology device may maintain focus on the sample, using the coarse filtered settings, while the sample and/or optical head is moved to effectively follow the topography of the sample while moving to a new measurement location. The fine filter settings may be used when there is no lateral movement, i.e., when the optics of the optical metrology device are aligned with the desired measurement location. Thus, once at the desired measurement location the optical metrology device may be focused on the sample using the fine filtering parameters. If desired, the use of the fine filter parameters may be delayed until the optical metrology device is in focus within a desired threshold using the course filter parameters.

Additionally, the raw focus signal is provided to a second filter 610, which is similar to filter 604, but uses different filter parameters. The second filter 610 receives coarse range filter parameters, e.g., on input terminal Course Range Settings. The output signal from the second filter 610 is compared to the output signal from the first filter 604 with comparator 612. By way of example, the comparator 612 may produce the absolute value of the difference between the filtered signals from filters 604 and 610. The output of the comparator 612 is provided to a range filter 614, which determines whether the difference between the two filtered focus signals is within a desired range. If the difference between the two filtered focus signals is within the desired range, then the filtered focus signal from filter 604 (and provided at Data Output) has little or no (i.e., less than the threshold range) mean amplitude displacement with respect to the filtered focus signal from filter 610 and accordingly, no mean amplitude displacement with respect to the raw focus signal. However, if the range finder 614 determines the difference between the two filtered focus signals is outside the desired range, then the filtered focus signal from the first filter 604 has a relatively large (i.e., greater than the threshold range) mean amplitude displacement with respect to the raw focus signal, which is an indication of relative lateral movement between the sample and optics. To ensure stability, a moving window of a desired size, e.g., 26 samples, may be used to determine whether the difference between the two filtered focus signals is within the desired threshold range.

The output of the range filter 614 is provided to the logic AND gate 608 along with an inverted stage move signal. When the difference between the two filtered focus signals from filters 604 and 610 is within a desired range and the stage is not moving, the logic AND gate 608 will provide a signal to switch 606, which causes switch 606 to provide the fine filter parameters to the first filter 604. Otherwise, the logic AND gate 608 will provide a signal to switch 606 that causes the switch 606 to provide the coarse filter parameters to the first filter 604. Thus, it can be seen that the coarse range filter parameters used by the second filter 610, as received on input terminal Coarse Range Settings, provides an indication of relative lateral movement between the sample and optics and functionally controls when to switch between the coarse filter settings and the fine filter settings for the first filter 604. The coarse range filter parameters used by filter 610 to identify lateral movement, are thus, in general, different than the coarse filter parameters used by filter 604 to produce a focus signal during lateral movement. For example, the coarse filter parameters used by filter 604 may provide a greater reduction in the amplitude of noise in the signal than the coarse range filter parameters used by filter 610. The coarse range filter parameters to be provided to filter 610 may be empirically chosen to provide desired sensitivity to lateral movement.

In addition, a third filter 616, comparators 618, and range filter 620, similar to second filter 610, comparator 612, and range finder 614 may be used. The third filter 616 may use fine range filter parameters provided on input terminal Fine Range Settings. The fine range filter parameters provided to filter 616 may be used to identify when the focus signal provided by first filter 604 using the fine filter parameters is adequately in focus. Thus, the fine range filter parameters used by filter 616 are, in general, different than the fine filter parameters used by filter 604. For example, the fine filter parameters used by filter 604 may provide a greater reduction in the amplitude of noise in the signal than the fine range filter parameters used by filter 616. The fine range filter parameters to be provided to filter 616 may be empirically chosen to provide desired sensitivity.

The output of the filter 616 is received by the comparator 618, which also receives the output of the filter 604. The comparator 618 compares the outputs of the two filters 604 and 616. The first filter 604 switches between coarse filter parameters and fine filter parameters, while the third filter 616 continually uses the fine range filter parameters. Accordingly, the outputs from the two filters 604 and 616 will have a relatively large difference until the filter 604 is using the fine filter parameters and there is sufficient time for the focus signal from filter 604 to settle, at which time the optical metrology device is in focus. The output of the comparator 618 is provided to the range filter 620, which determines whether the difference between the two filtered focus signals is within a desired range. If the range finder 620 determines the difference between the two filtered focus signals is outside a desired range, then the filtered focus signal from filter 604 has a relatively large mean amplitude displacement with respect to the filtered focus signal from filter 616 and accordingly, a relatively large mean amplitude displacement with respect to the raw focus signal. Accordingly, the range filter 620 provides an output signal at terminal Fine In_Focus indicating that the optical metrology device is not in focus and the autofocus enabler 516 (FIG. 7) allows the autofocus operation to continue. However, if the range finder 620 determines the difference between the two filtered focus signals is within the desired range, then the filtered focus signal from filter 604 has little or no mean amplitude displacement with respect to the raw focus signal, and accordingly, the range filter 614 provides an output signal at terminal Fine In_Focus indicating that the optical metrology device is in focus and the autofocus enabler 516 (FIG. 7) disables the autofocus operation. Again, to ensure stability, a moving window of a desired size, e.g., 26 samples, may be used to determine whether the difference between the two filtered focus signals is within the desired threshold range.

Figure 1:
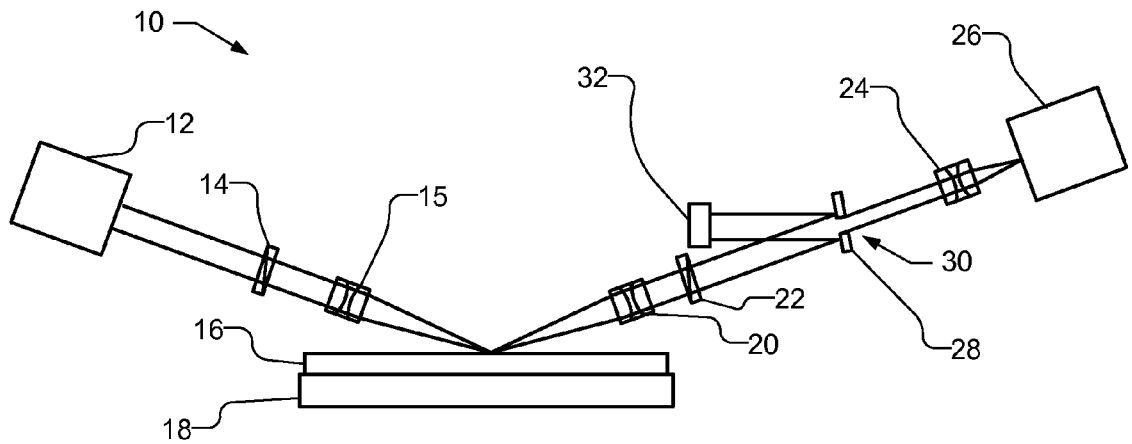
FIG. 1 illustrates an ellipsometer with a conventional focusing system.
Figure 9:
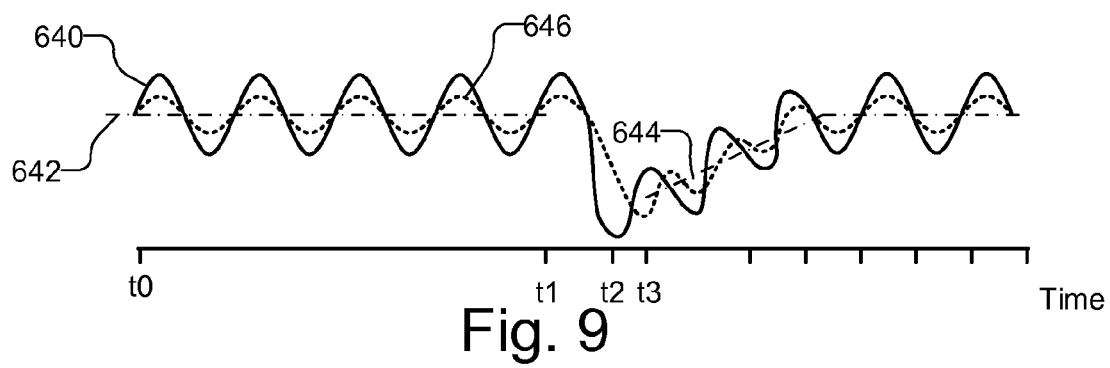
FIG. 9 illustrates an idealized raw focus signal and filtered focus signal.

FIG. 9, by way of example, illustrates an idealized raw focus signal 640 from a focus system, such as focus system 150 shown in FIG. 1. The raw focus signal 640 is illustrated with periodic noise, which is caused by, e.g., the rotating optics in focus system 150. It should be understood, that other or different noise may be present in the raw focus signal 640 including noise that is not periodic. When the focusing system is properly in focus, the raw focus signal 640 will be centered on a zero value 642 determined during calibration, illustrated by a dot-dash line. Thus, while the periodic noise illustrated in FIG. 9 causes the raw focus signal 640 to rise above and fall below the zero value 642, there is no offset, i.e., there no mean amplitude displacement, with respect to the calibrated zero value 642, as illustrated from time t0 to t1.

When there is a deviation from the desired (or best) focusing position, e.g., when the sample and/or optics of the optical metrology device begin to move laterally, the raw focus signal 640 may incur a large offset, i.e., mean amplitude displacement, with respect to the previous zero value 642, as illustrated at time t2. Once the focusing system is again properly focused, the raw focus signal 640 will again be centered on a zero value 644, illustrated by dot-dash line starting at time t3. The focusing system may maintain focus on the sample, even while the sample and/or optics of the optical metrology device continue to move laterally, so that the focusing system follows the topography of the sample, which is illustrated by the lack of an offset, i.e., mean amplitude displacement, between the raw focus signal 640 and the zero value 644, after time t3.

Also illustrated in FIG. 9 is an example of a filtered focus signal 646, which is generated by filtering the raw focus signal 640 to reduce the amplitude to noise while preserving edges, e.g., illustrated between times t1 and t2. By way of example, the filter 604 shown in FIG. 8 may be used to produce the filtered focus signal 646. The settings of the Kalman filter, or other similar filters, may be adjusted to filter the raw focus signal 640 to weakly reduce the amplitude of the noise (sometimes referred to herein as a coarse filter) at certain times, e.g., when there is lateral movement, or strongly reduce the amplitude of the noise (sometimes referred to herein as a fine filter) to preserve the edges. As illustrated in FIG. 9, the filtered focus signal 646 between time t0 to time t1 is similar to the raw focus signal 640, but with reduced amplitude. Accordingly, the filtered focus signal 646 has no mean amplitude displacement with respect to the raw focus signal 640 or the zero value 642. As illustrated in FIG. 9, however, the filtered focus signal 646 has a lag when the raw focus signal 640 has a large deviation, e.g., illustrated between times t1 and t2. The lag between the filtered focus signal 646 and the raw focus signal 640 is a function of the strength of the filter, e.g., a coarse filter will produce relatively little lag, while a fine filter will produce a greater amount of lag. Consequently, as illustrated in FIG. 9, between times t1 and t3, the filtered focus signal 646 has a relatively large offset with respect to the raw focus signal 640. At time t3, the filtered focus signal 646 is again centered on the raw focus signal 640, i.e., there is little or no mean amplitude displacement, and thus, the center value, i.e., zero value 644. Consequently, it can be seen that the offset or mean amplitude displacement between the filtered focus signal 646 and the raw focus signal 640 is an accurate indication of whether raw focus signal 640 is centered on the zero value 642 or 644 and thus, whether the optical metrology device is in focus (little or no deviation from the desired (or best) focusing position). Similarly, by comparing a finely filtered focus signal, which has a strongly reduced amplitude but increased lag, with respect to a coarsely filtered focus signal, which has a weakly reduced amplitude with little lag, it is possible to similarly determine whether the raw focus signal 640 is centered on the zero value 642 or 644 and thus, whether focusing system is in focus (little or no deviation from the desired (or best) focusing position).

Figure 10A:
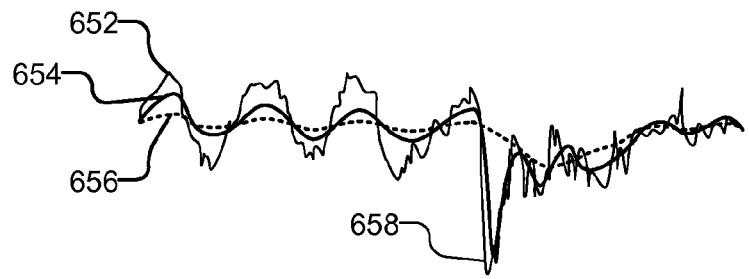
FIG. 10A illustrates a raw focus signal, a coarse filtered focus signal, and a fine filtered focus signal.

FIG. 10A illustrates an example of a raw focus signal 652, a relatively coarsely filtered focus signal 654 and a relatively finely filtered focus signal 656, e.g., the coarsely filtered focus signal 654 is referred to as "coarsely" in a relative sense as it is more coarsely filtered than the finely filtered focus signal 656. The coarsely filtered focus signal 654 may be produced, e.g., by filter 610 using the coarse range filter parameters, and the finely filtered focus signal 656 may be produced by filter 604 using fine filter parameters (or using the course filter parameters). Similarly, the coarsely filtered focus signal 654 may be produced by filter 616 using the fine range filter parameters and the finely filtered focus signal 656 may be produced by filter 604 using fine filter parameters. As can be seen in FIG. 10A, both the coarsely filtered focus signal 654 and finely filtered focus signal 656 have reduced the noise in focus signal 652 without producing a phase delay, however, finely filtered focus signal 656 has an increased lag with respect to the raw focus signal 652 than coarsely filtered focus signal 654 when there is a large displacement in the raw focus signal 652, e.g., at peak 662.

Figure 10B:
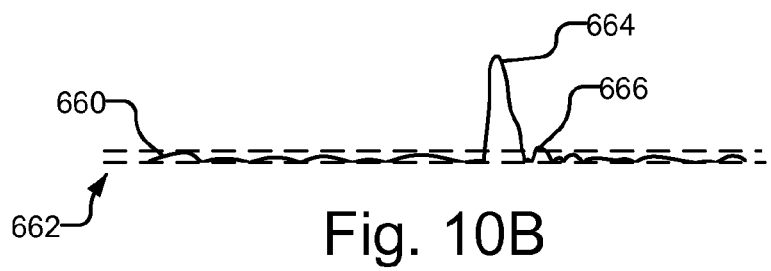
FIG. 10B illustrates the absolute value of the difference between the coarse filtered focus signal and the fine filtered focus signal from FIG. 10A and a range threshold.

FIG. 10B illustrates a signal 660 that is the absolute value of the difference between the coarsely filtered focus signal 654 and the finely filtered focus signal 656, e.g., such as that as may be produced by comparator 612 (or similarly by comparator 618). Additionally, FIG. 10B illustrates a range threshold 662, such as that used by range filter 614 (or similarly by range filter 620), to determine when the finely filtered focus signal 656 has no offset, i.e., no mean amplitude displacement, with respect to the raw focus signal 652. As can be seen in FIG. 10B, spikes 664 and 666 exceed the range threshold 662 and therefore indicate that there is large offset between the coarsely filtered focus signal 654 and the raw focus signal 652. As can be seen, by adjusting the range threshold 662, the sensitivity to offset may be appropriately adjusted. Moreover, by adjusting the range filter parameters used by filter 610 (or filter 616), the difference in the lag between the coarsely filtered focus signal 654 and the finely filtered focus signal 656 may be controlled thereby adjusting the magnitude of the mean amplitude displacement may be adjusted. Additionally, to avoid instability caused by separate spikes 664 and 666, a moving window of a desired size, e.g., 26 samples, may be used to determine whether the difference between the two filtered focus signals is within the desired threshold range.

Figure 11:
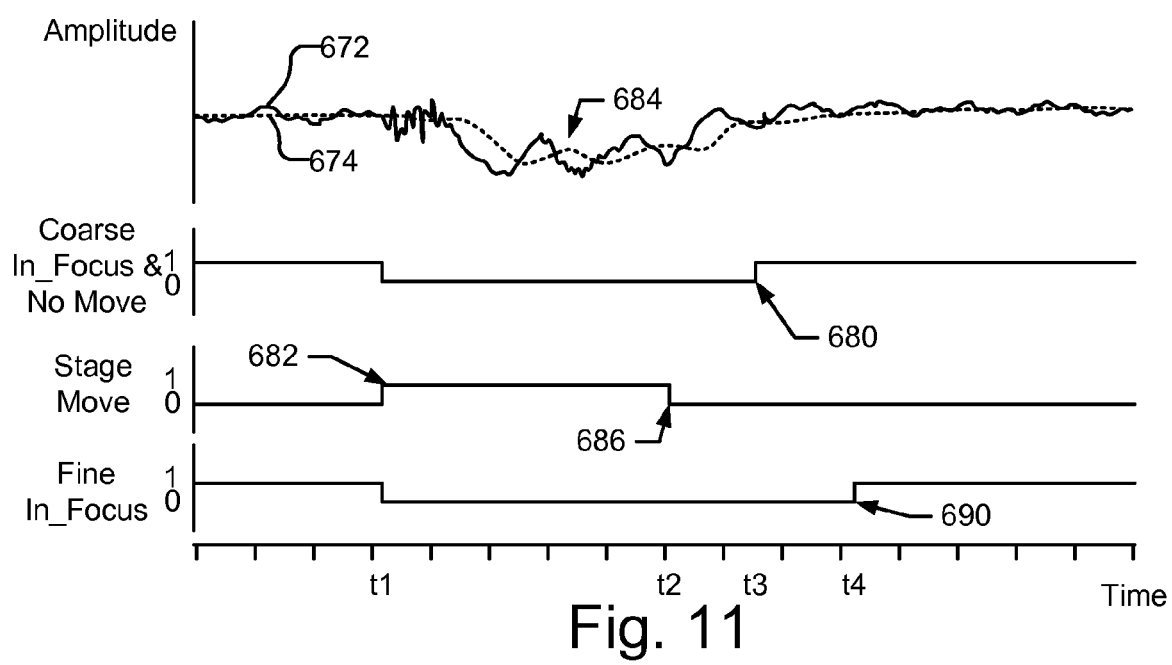
FIG. 11 illustrates several waveforms used in the closed loop control of the autofocus system for the optical metrology device.

FIG. 11 illustrates several waveforms used in the closed loop control of the autofocus system for the optical metrology device. The waveforms illustrate the amplitude of a raw focus signal 672 (which may be received at terminal Data Input in FIG. 8) and a filtered focus signal 674 (which may be provided at terminal Data Output in FIG. 8) with respect to time. Additionally, waveforms illustrate a digital signal (labeled Coarse In_focus & No Move) indicating whether the coarse filtered focus signal from filter 604 is offset with respect to the focus signal and the stage is not moving (which may be produced by logic AND gate 608 in FIG. 8), a digital signal (labeled Stage Move) indicating whether the stage is moving (which may be received at terminal Stage Move in FIG. 8), and a digital signal (labeled Fine In_Focus) indicating whether the fine filtered focus signal from filter 604 is offset with respect to the focus signal (which may be provided at terminal Fine In_Focus in FIG. 8).

FIG. 11 illustrates the system starting in an "in focus" state (Fine In_Focus is high) and the stage is not moving (Stage Move is low), which would be expected when the optical metrology device is aligned and performing metrology at a measurement site on the sample. Because the Fine In_Focus signal is high, the autofocus enabler 516 (FIG. 7) may disable vertical movement. At time t1, the stage begins lateral movement, e.g., in the X Y directions, to move to a new measurement site (Stage Move is high at edge 682), causing the Fine In_Focus signal to switch from a high state to a low state, which causes the autofocus enabler 516 (FIG. 7) to enable vertical movement to permit focusing adjustment. Additionally, the high state of the Stage Move signal causes the Coarse In_Focus & No Move signal produced by logic AND gate 608 to switch from a high state to a low state and, thus, switch 606 in FIG. 8 will cause the course filter parameters on the Course Settings input terminal to be provided to the filter 604. Thus, the filter 604 uses the coarse filter parameters to provide a coarse filter signal at the Data Output terminal in FIG. 8, which the focus system uses to adjust the focal position of the optical metrology device during the lateral movement.

At time t2, the measurement location is aligned with the optical metrology device, and the stage stops moving, and the Stage Move waveform transitions to a low state at edge 686. The Coarse In_Focus & No Move signal produced by logic AND gate 608, however, remains low until the range finder 614 determines that the difference between the filtered focus signals produced by filter 604 using the coarse filter parameters and the filter 610 using the coarse range filter parameters is within the desired range, indicating that the coarse filter signal produced by filter 604 has little or no mean amplitude displacement with respect to the raw focus signal. When the difference between filtered focus signals is within the desired range as provided by range finder 614 at time t3, the Coarse In_Focus & No Move signal produced by logic AND gate 608 transitions high, e.g., at edge 680, and, thus, switch 606 in FIG. 8 will cause the fine filter parameters on the Fine Settings input terminal to be provided to the filter 604. The Fine In_Focus signal, however, remains low until the range finder 620 determines that the difference between the filtered focus signals from filter 604 using the fine filter parameters and filter 616 using the fine range filter parameters is within the desired range, indicating that the fine filter signal produced by filter 604 has little or no mean amplitude displacement with respect to the raw focus signal. When the difference between filtered focus signals is within the desired range as provided by range finder 620 at time t4, the Fine In_Focus signal transitions high, e.g., at edge 690, causing the autofocus enabler 516 (FIG. 7) to disable the adjustment of the focal position of the optical metrology device to prevent any unnecessary motion while the optical metrology device measures the sample at the new measurement location.

If desired, the same focus system may be used in an open loop control of the focal position of the optical metrology device, i.e., where the optical metrology device is not focused during lateral movement. During open loop control, the adjustment of the focal position does not occur until the stage stops moving at edge 686 on the Stage Move waveform. The adjustment of the focal position may then be performed as discussed above, e.g., using a coarse filter signal until the Coarse In_Focus & No Move signal transitions high, e.g., at edge 680, and then using the fine filter signal until the Fine In_Focus signal transitions high, e.g., at edge 690, then disabling adjustment of the focal position until at the next measurement site.

Figure 12:
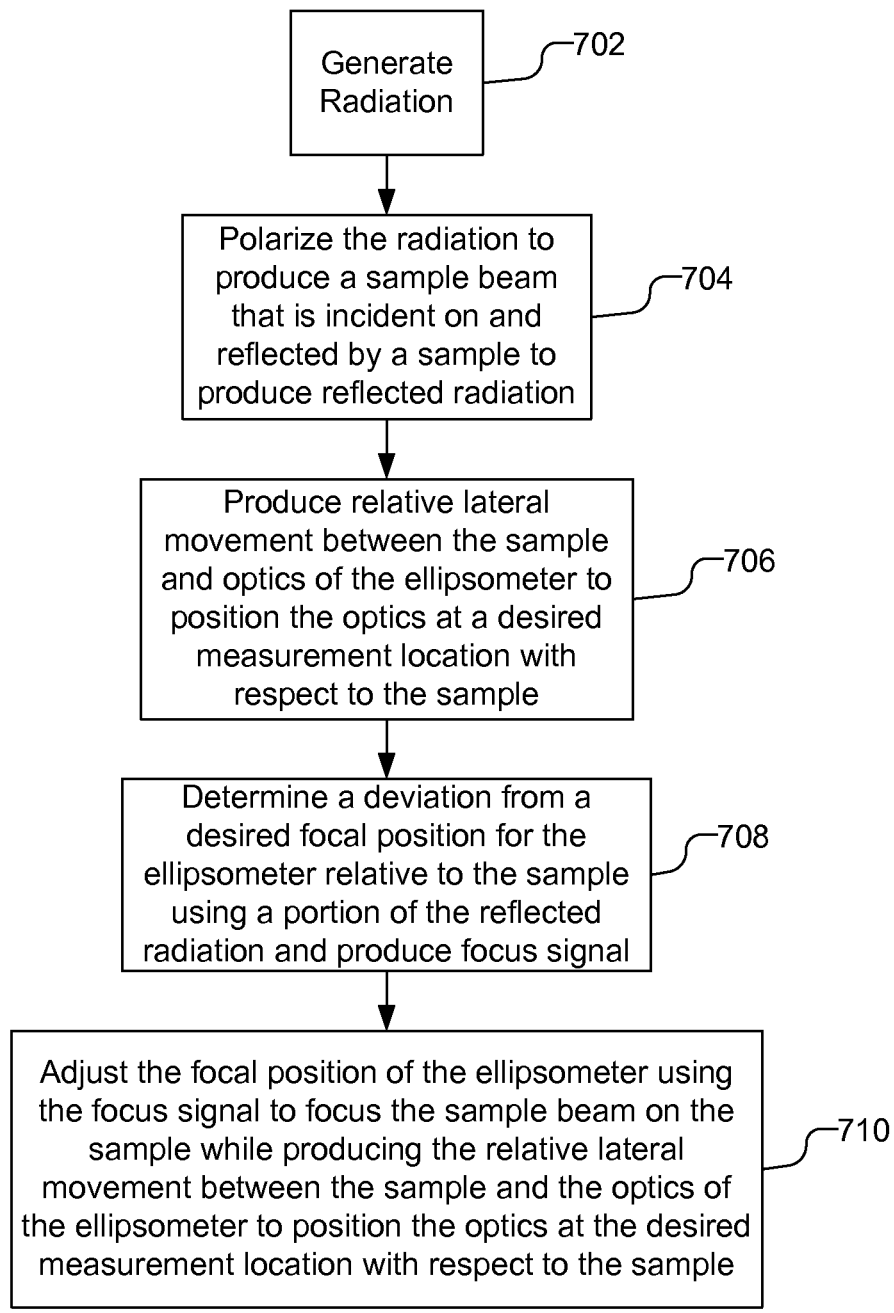
FIG. 12 is a flow chart illustrating a method of focusing an ellipsometer while there is movement to align the ellipsometer to a measurement location.

FIG. 12 is a flow chart illustrating a method of focusing an ellipsometer in accordance to one embodiment. As illustrated, radiation is generated (702) and the radiation is polarized to produce a sample beam that is incident on and reflected by a sample to produce reflected radiation (704). Relative lateral movement between the sample and optics of the ellipsometer are produced in order to position the optics at a desired measurement location with respect to the sample (706). The deviation from a desired focal position for the ellipsometer relative to the sample is determined using a portion of the reflected radiation and a focus signal is generated (708), which may be performed, e.g., as discussed above. For example, a portion of the reflected radiation may be focused into a spot on a two-dimensional sensor, and a location of the spot on the two-dimensional sensor determined, which is used to determine the deviation from the desired focal position. The focal position of the ellipsometer is adjusted based on the focus signal to focus the sample beam on the sample while producing the relative lateral movement between the sample and the optics of the ellipsometer to position the optics at the desired measurement location with respect to the sample (710). Thus, the ellipsometer is placed at the desired focal position with respect to the sample during the relative lateral movement between the sample and the optics of the ellipsometer. As discussed above, determining the deviation from the desired focal position and adjusting the focal position of the ellipsometer may be performed using a closed loop control. Additionally, after the optics of the ellipsometer are positioned at the desired measurement location with respect to the sample, i.e., when the lateral movement stops, the adjustment of the focal position of the ellipsometer is stopped.

Figure 13:
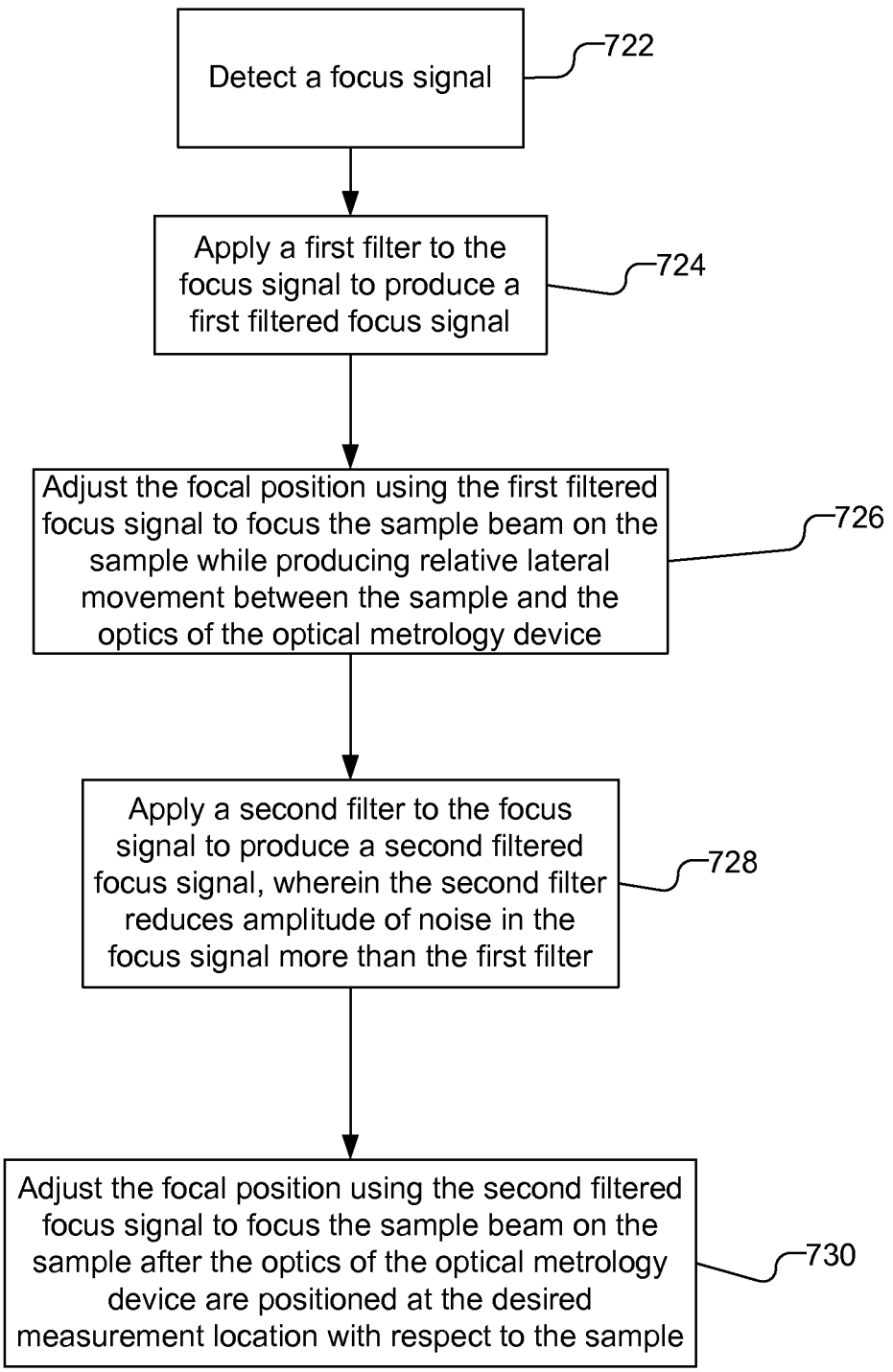
FIG. 13 is a flow chart illustrating a method of determining deviation from a desired focal position and adjusting the focal position.

FIG. 13 is a flow chart illustrating a method of adjusting the focal position. As illustrated, a focus signal is detected, e.g., using a portion of the reflected radiation (722). A first filter is applied to the focus signal to produce a first filtered focus signal (724). The focal position of the optical metrology device, e.g., the ellipsometer referred to in FIG. 12, or other metrology device, is adjusted using the first filtered focus signal to focus the sample beam on the sample while producing relative lateral movement between the sample and the optics of the optical metrology device (726). Additionally, a second filter is applied to the focus signal to produce a second filtered focus signal (728). The second filter reduces the amplitude of noise in the focus signal more than the first filter. Thus, the first filter may be considered a coarse filter while the second filter may be considered a fine filter. The focal position of the optical metrology device may be adjusted using the second filtered focus signal to focus the sample beam on the sample after the optics of the optical metrology device are positioned at the desired measurement location with respect to the sample (730). Once the optics of the optical metrology device are positioned at the desired measurement location with respect to the sample, the method may further include determining when a mean amplitude displacement between the first filtered focus signal and the focus signal is within a threshold range, wherein applying the second filter to the focus signal (728) and adjusting the focal position of the ellipsometer using the second filtered focus signal (730) are performed when the mean amplitude displacement between the first filtered focus signal and the focus signal is within the threshold range. Determining when the mean amplitude displacement between the first filtered focus signal and the focus signal is within the threshold range may include applying a third filter to the focus signal to produce a third filtered focus signal, wherein the first filter reduces the amplitude of noise in the focus signal more than the third filter; determining an absolute value of a difference between the first filtered focus signal and the third filtered focus signal and determining that the absolute value is within the threshold range. Additionally, after the optics of the optical metrology device are positioned at the desired measurement location with respect to the sample, the method may further include determining when a mean amplitude displacement between the second filtered focus signal and the focus signal is within a threshold range and disabling adjustment of the focal position of the optical metrology device when the mean amplitude displacement between the second filtered focus signal and the focus signal is within the threshold range. Determining when the mean amplitude displacement between the second filtered focus signal and the focus signal is within the threshold range may include applying a third filter to the focus signal to produce a third filtered focus signal, wherein the second filter reduces the amplitude of noise in the focus signal more than the third filter; determining an absolute value of a difference between the second filtered focus signal and the third filtered focus signal, and determining that the absolute value is within the threshold range.

Figure 14:
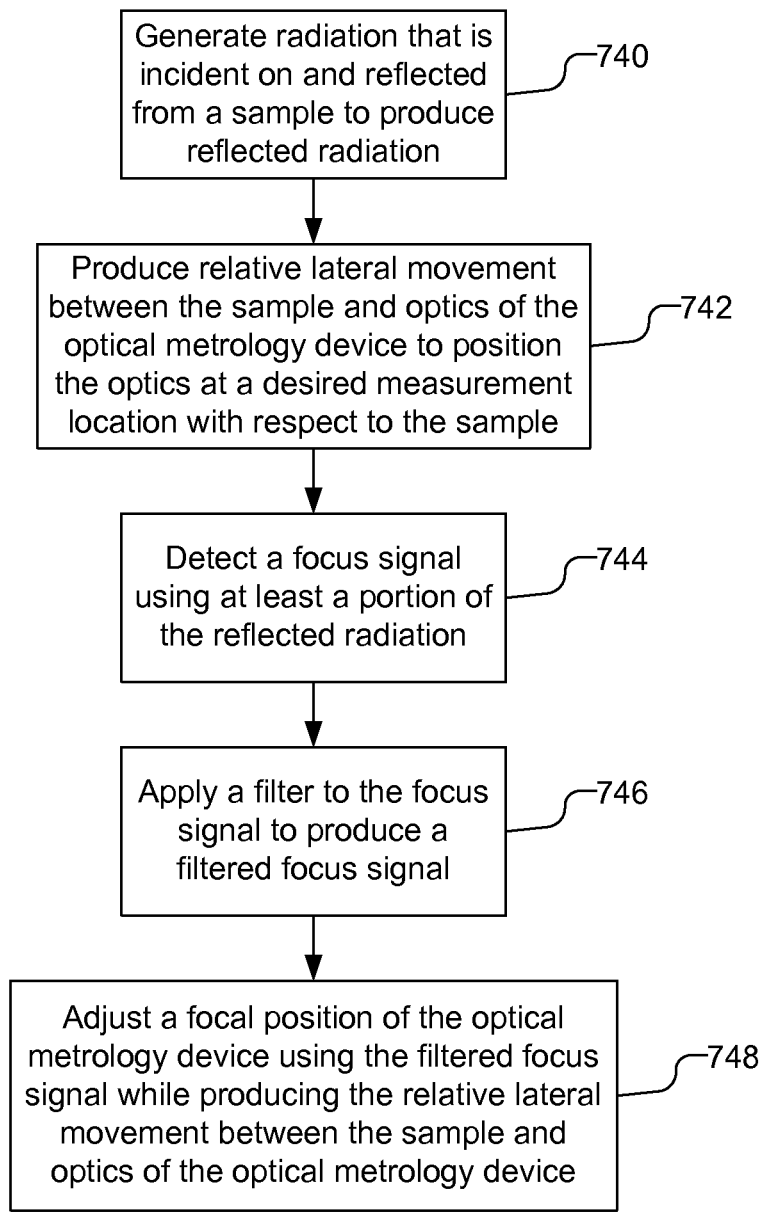
FIG. 14 is a flow chart illustrates a method of focusing an optical metrology device using a filter, e.g., in a closed loop control.

FIG. 14 is a flow chart illustrating another embodiment of a method of focusing an optical metrology device. As illustrated, radiation is generated that is incident on and reflected from a sample to produce reflected radiation (740).

Relative lateral movement is produced between the sample and optics of the optical metrology device to position the optics at a desired measurement location with respect to the sample (742). A focus signal is detected using at least a portion of the reflected radiation (744) and a filter is applied to the focus signal to produce a filtered focus signal (746). The filter may be a bilateral filter. The focal position of the optical metrology device is adjusted using the filtered focus signal while producing the relative lateral movement between the sample and optics of the optical metrology device (748). The adjustment of the focal position of the optical metrology device using the filtered focus signal while producing the relative lateral movement between the sample and optics of the optical metrology device is performed with a closed loop control. As discussed in FIG. 13, the filter may be a first filter producing a first filtered focus signal so that while producing the relative lateral movement between the sample and optics of the optical metrology device the focal position of the optical metrology device is adjusted using the first filtered focus signal and the method may further include applying a second filter to the focus signal to produce a second filtered focus signal, wherein the second filter reduces amplitude of noise in the focus signal more than the first filter and adjusting the focal position of the optical metrology device using the second filtered focus signal after the optics of the optical metrology device are positioned at the desired measurement location with respect to the sample. As discussed above, after the optics of the optical metrology device are positioned at the desired measurement location with respect to the sample, the method may include determining when a mean amplitude displacement between the first filtered focus signal and the focus signal is within a threshold range, wherein applying the second filter to the focus signal and adjusting the focal position of the optical metrology device using the second filtered focus signal are performed when the mean amplitude displacement between the first filtered focus signal and the focus signal is within the threshold range. Determining when the mean amplitude displacement between the first filtered focus signal and the focus signal is within the threshold range may include applying a third filter to the focus signal to produce a third filtered focus signal, wherein the first filter reduces the amplitude of noise in the focus signal more than the third filter, determining an absolute value of a difference between the first filtered focus signal and the third filtered focus signal and determining that the absolute value is within the threshold range. Additionally, after the optics of the optical metrology device are positioned at the desired measurement location with respect to the sample, the method may further include determining when a mean amplitude displacement between the second filtered focus signal and the focus signal is within a threshold range and disabling adjustment of the focal position of the optical metrology device when the mean amplitude displacement between the second filtered focus signal and the focus signal is within the threshold range. Determining when the mean amplitude displacement between the second filtered focus signal and the focus signal is within the threshold range may include applying a third filter to the focus signal to produce a third filtered focus signal, wherein the second filter reduces the amplitude of noise in the focus signal more than the third filter, determining an absolute value of a difference between the second filtered focus signal and the third filtered focus signal, and determining that the absolute value is within the threshold range. The radiation that is incident on and reflected from the sample to produce the reflected radiation may be the sample beam used by the optical metrology device for measurement of one or more characteristics of the sample and the focus signal may include periodic noise that is filtered by the filter to produce the filtered focus signal.

Figure 15:
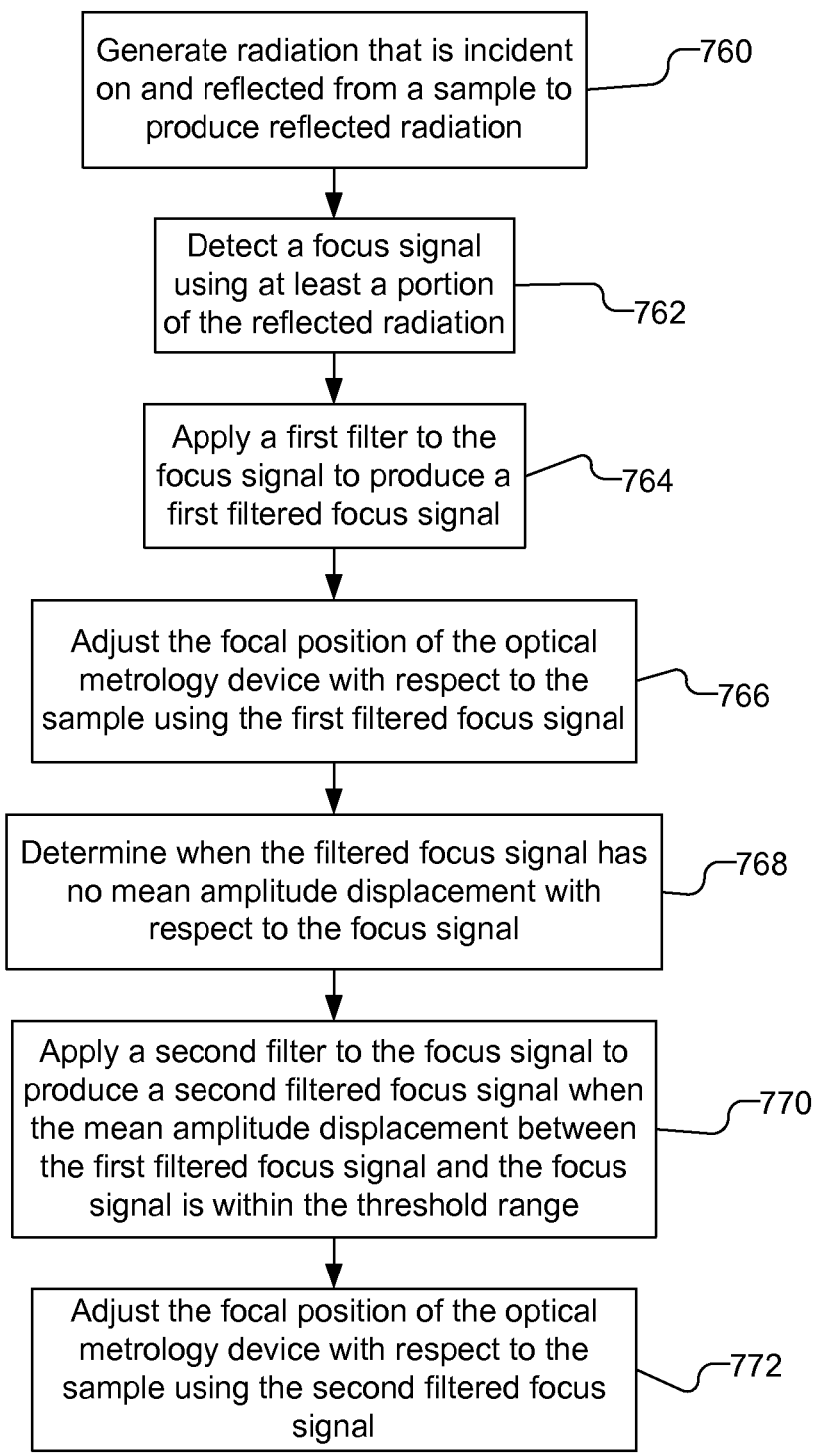
FIG. 15 is a flow chart illustrating a method of focusing an optical metrology device using a filter, e.g., in open loop control.

FIG. 15 is another flow chart illustrating a method of focusing an optical metrology device. As illustrated, radiation is generated that is incident on and reflected from a sample to produce reflected radiation (760) and a focus signal is detected using at least a portion of the reflected radiation (762). A first filter is applied to the focus signal to produce a first filtered focus signal (764). The focal position of the optical metrology device is adjusted with respect to the sample using the first filtered focus signal (766). It is determined when a mean amplitude displacement between the first filtered focus signal and the focus signal is within a threshold range (768). A second filter is applied to the focus signal to produce a second filtered focus signal when the mean amplitude displacement between the first filtered focus signal and the focus signal is within the threshold range (770). The second filter reduces amplitude of noise in the focus signal more than the first filter. The focal position of the optical metrology device is adjusted using the second filtered focus signal to focus the sample beam on the sample (772). Applying the first filter to the focus signal comprises using a Kalman filter with first filter parameters and applying the second filter to the focus signal comprises using the Kalman filter with second filter parameters. As discussed above, determining when the mean amplitude displacement between the first filtered focus signal and the focus signal is within the threshold range may include applying a third filter to the focus signal to produce a third filtered focus signal, wherein the first filter reduces the amplitude of noise in the focus signal more than the third filter, determining an absolute value of a difference between the first filtered focus signal and the third filtered focus signal, and determining that the absolute value is within the threshold range. Additionally, it may be determined when a mean amplitude displacement between the second filtered focus signal and the focus signal is within a second threshold range; and adjustment of the focal position of the optical metrology device disabled when the mean amplitude displacement between the second filtered focus signal and the focus signal is within the second threshold range. In an open loop system, relative lateral movement between the sample and optics of the optical metrology device is produced to position the optics at a desired measurement location with respect to the sample, wherein adjusting the focal position of the optical metrology device with respect to the sample using the first filtered focus signal is performed only after the optics of the optical metrology device are positioned at the desired measurement location with respect to the sample. In a closed loop system, relative lateral movement between the sample and optics of the optical metrology device is produced to position the optics at a desired measurement location with respect to the sample, wherein applying a first filter to the focus signal and adjusting the focal position of the optical metrology device with respect to the sample using the first filtered focus signal are performed during the relative lateral movement and applying the second filter to the focus signal to produce the second filtered focus signal when the mean amplitude displacement between the first filtered focus signal and the focus signal is within the threshold range and adjusting the focal position of the optical metrology device using the second filtered focus signal are performed only after the optics of the optical metrology device are positioned at the desired measurement location with respect to the sample. The radiation that is incident on and reflected from the sample to produce the reflected radiation is a sample beam used by the optical metrology device for measurement of one or more characteristics of the sample and wherein the focus signal comprises periodic noise that is filtered by the first filter to produce the first filtered focus signal and filtered by the second filter to produce the second filtered focus signal.

Although the present invention is illustrated in connection with specific embodiments for instructional purposes, the present invention is not limited thereto. Various adaptations and modifications may be made without departing from the scope of the invention. Therefore, the spirit and scope of the appended claims should not be limited to the foregoing description.

What is claimed is:

1. A method of focusing an ellipsometer, the method comprising:
   generating radiation;
   polarizing the radiation to produce a sample beam that is incident on and reflected by a sample to produce reflected radiation;
   producing relative lateral movement between the sample and optics of the ellipsometer to position the optics at a desired measurement location with respect to the sample;
   determining a deviation from a desired focal position for the ellipsometer relative to the sample using a portion of the reflected radiation received while producing the relative lateral movement between the sample and the optics and generating a focus signal;
   applying a first filter to the focus signal to produce a first filtered focus signal;
   adjusting a focal position of the ellipsometer using the first filtered focus signal to focus the sample beam on the sample while producing the relative lateral movement between the sample and the optics of the ellipsometer;
   applying a second filter to the focus signal to produce a second filtered focus signal, wherein the second filter reduces amplitude of noise in the focus signal more than the first filter; and
   adjusting the focal position of the ellipsometer based using the second filtered focus signal to focus the sample beam on the sample after the optics of the ellipsometer are positioned at the desired measurement location with respect to the sample.

2. The method of claim 1, wherein determining the deviation from the desired focal position and adjusting the focal position of the ellipsometer using the first filtered focus signal is performed using a closed loop control.

3. The method of claim 1, wherein the ellipsometer is placed at the desired focal position with respect to the sample during the relative lateral movement between the sample and the optics of the ellipsometer.

4. The method of claim 1, further comprising disabling the adjustment of the focal position of the ellipsometer after the optics of the ellipsometer are positioned at the desired measurement location with respect to the sample.

5. The method of claim 1, wherein applying the first filter to the focus signal to produce a first filtered focus signal comprises using a bilateral filter to filter noise from the focus signal.

6. The method of claim 1, wherein applying the first filter to the focus signal comprises using a Kalman filter with first filter parameters and applying the second filter to the focus signal comprises using the Kalman filter with second filter parameters.

7. The method of claim 1, wherein after the optics of the ellipsometer are positioned at the desired measurement location with respect to the sample, the method further comprises:
   determining when a mean amplitude displacement between the first filtered focus signal and the focus signal is within a threshold range;
   wherein applying the second filter to the focus signal and adjusting the focal position of the ellipsometer using the second filtered focus signal are performed when the mean amplitude displacement between the first filtered focus signal and the focus signal is within the threshold range.

8. The method of claim 7, wherein determining when the mean amplitude displacement between the first filtered focus signal and the focus signal is within the threshold range comprises:
   applying a third filter to the focus signal to produce a third filtered focus signal, wherein the first filter reduces the amplitude of noise in the focus signal more than the third filter;
   determining an absolute value of a difference between the first filtered focus signal and the third filtered focus signal; and
   determining that the absolute value is within the threshold range.

9. The method of claim 1, wherein after the optics of the ellipsometer are positioned at the desired measurement location with respect to the sample, the method further comprises:
   determining when a mean amplitude displacement between the second filtered focus signal and the focus signal is within a threshold range; and
   disabling adjustment of the focal position of the ellipsometer when the mean amplitude displacement between the second filtered focus signal and the focus signal is within the threshold range.

10. The method of claim 9, wherein determining when the mean amplitude displacement between the second filtered focus signal and the focus signal is within the threshold range comprises:
    applying a third filter to the focus signal to produce a third filtered focus signal, wherein the second filter reduces the amplitude of noise in the focus signal more than the third filter;
    determining an absolute value of a difference between the second filtered focus signal and the third filtered focus signal; and
    determining that the absolute value is within the threshold range.

11. A method of focusing an optical metrology device, the method comprising:
    generating radiation that is incident on and reflected from a sample to produce reflected radiation;
    producing relative lateral movement between the sample and optics of the optical metrology device to position the optics at a desired measurement location with respect to the sample;
    detecting a focus signal using at least a portion of the reflected radiation;
    applying a first filter to the focus signal to produce a first filtered focus signal;
    adjusting a focal position of the optical metrology device based on the first filtered focus signal while producing the relative lateral movement between the sample and the optics of the optical metrology device;

applying a second filter to the focus signal to produce a second filtered focus signal, wherein the second filter reduces amplitude of noise in the focus signal more than the first filter; and adjusting the focal position of the optical metrology device using the second filtered focus signal to focus the radiation on the sample after the optics of the optical metrology device are positioned at the desired measurement location with respect to the sample.

12. The method of claim 11, wherein applying the first filter and applying the second filter uses a bilateral filter.

13. The method of claim 11, wherein detecting the focus signal, applying the first filter, and adjusting the focal position of the optical metrology device using the first filtered focus signal while producing the relative lateral movement between the sample and the optics of the optical metrology device is performed with a closed loop control.

14. The method of claim 11, wherein applying the first filter to the focus signal comprises using a Kalman filter with first filter parameters and applying the second filter to the focus signal comprises using the Kalman filter with second filter parameters.

15. The method of claim 11, wherein after the optics of the optical metrology device are positioned at the desired measurement location with respect to the sample, the method further comprises:
    determining when a mean amplitude displacement between the first filtered focus signal and the focus signal is within a threshold range;
    wherein applying the second filter to the focus signal and adjusting the focal position of the optical metrology device using the second filtered focus signal are performed when the mean amplitude displacement between the first filtered focus signal and the focus signal is within the threshold range.

16. The method of claim 15, wherein determining when the mean amplitude displacement between the first filtered focus signal and the focus signal is within the threshold range comprises:
    applying a third filter to the focus signal to produce a third filtered focus signal, wherein the first filter reduces the amplitude of noise in the focus signal more than the third filter;
    determining an absolute value of a difference between the first filtered focus signal and the third filtered focus signal; and
    determining that the absolute value is within the threshold range.

17. The method of claim 11, wherein after the optics of the optical metrology device are positioned at the desired measurement location with respect to the sample, the method further comprises:
    determining when a mean amplitude displacement between the second filtered focus signal and the focus signal is within a threshold range; and
    disabling adjustment of the focal position of the optical metrology device when the mean amplitude displacement between the second filtered focus signal and the focus signal is within the threshold range.

18. The method of claim 17, wherein determining when the mean amplitude displacement between the second filtered focus signal and the focus signal is within the threshold range comprises:
    applying a third filter to the focus signal to produce a third filtered focus signal, wherein the second filter reduces the amplitude of noise in the focus signal more than the third filter;
    determining an absolute value of a difference between the second filtered focus signal and the third filtered focus signal; and
    determining that the absolute value is within the threshold range.

19. The method of claim 11, wherein the optical metrology device is an ellipsometer.

20. The method of claim 11, wherein the radiation that is incident on and reflected from the sample to produce the reflected radiation is a sample beam used by the optical metrology device for measurement of one or more characteristics of the sample and wherein the focus signal comprises periodic noise that is filtered by applying the first filter to produce the first filtered focus signal.

21. A method of focusing an optical metrology device, the method comprising:
    generating radiation that is incident on and reflected from a sample to produce reflected radiation;
    detecting a focus signal using at least a portion of the reflected radiation;
    applying a first filter to the focus signal to produce a first filtered focus signal, wherein the first filter reduces an amplitude of noise in the focus signal;
    adjusting a focal position of the optical metrology device with respect to the sample using the first filtered focus signal;
    determining when a mean amplitude displacement between the first filtered focus signal and the focus signal is within a threshold range;
    applying a second filter to the focus signal to produce a second filtered focus signal when the mean amplitude displacement between the first filtered focus signal and the focus signal is within the threshold range, wherein the second filter reduces the amplitude of noise in the focus signal more than the first filter; and
    adjusting the focal position of the optical metrology device using the second filtered focus signal to focus the radiation on the sample.

22. The method of claim 21, wherein applying the first filter to the focus signal comprises using a Kalman filter with first filter parameters and applying the second filter to the focus signal comprises using the Kalman filter with second filter parameters.

23. The method of claim 21, wherein determining when the mean amplitude displacement between the first filtered focus signal and the focus signal is within the threshold range comprises:
    applying a third filter to the focus signal to produce a third filtered focus signal, wherein the first filter reduces the amplitude of noise in the focus signal more than the third filter;
    determining an absolute value of a difference between the first filtered focus signal and the third filtered focus signal; and
    determining that the absolute value is within the threshold range.

24. The method of claim 21, the method further comprises:
    determining when a mean amplitude displacement between the second filtered focus signal and the focus signal is within a second threshold range; and
    disabling adjustment of the focal position of the optical metrology device when the mean amplitude displacement between the second filtered focus signal and the focus signal is within the second threshold range.

25. The method of claim 21, further comprising:
producing relative lateral movement between the sample and optics of the optical metrology device to position the optics at a desired measurement location with respect to the sample, wherein adjusting the focal position of the optical metrology device with respect to the sample using the first filtered focus signal is performed only after the optics of the optical metrology device are positioned at the desired measurement location with respect to the sample.

26. The method of claim 21, further comprising:
producing relative lateral movement between the sample and optics of the optical metrology device to position the optics at a desired measurement location with respect to the sample;
wherein applying a first filter to the focus signal and adjusting the focal position of the optical metrology device with respect to the sample using the first filtered focus signal are performed during the relative lateral movement;
wherein applying the second filter to the focus signal to produce the second filtered focus signal when the mean amplitude displacement between the first filtered focus signal and the focus signal is within the threshold range and adjusting the focal position of the optical metrology device using the second filtered focus signal are performed only after the optics of the optical metrology device are positioned at the desired measurement location with respect to the sample.

27. The method of claim 21, wherein the optical metrology device is an ellipsometer.

28. The method of claim 21, wherein the radiation that is incident on and reflected from the sample to produce the reflected radiation is a sample beam used by the optical metrology device for measurement of one or more characteristics of the sample and wherein the focus signal comprises periodic noise that is filtered by the first filter to produce the first filtered focus signal and filtered by the second filter to produce the second filtered focus signal.

29. An optical metrology device comprising:
a source that emits radiation;
optics that cause the radiation to be incident on and reflected by a sample;
a detector positioned to receive the reflected radiation;
an actuator for adjusting a focal position of the optics with respect to the sample; and
a focusing system positioned to receive at least a portion of the reflected radiation and coupled to the actuator for altering the focal position of the optics with respect to the sample, the focusing system comprising:
a detector receives the at least the portion of the reflected radiation and produces a focus signal;
a first filter that filters the focus signal to produce a first filtered focus signal, wherein the first filter reduces an amplitude of noise in the focus signal, wherein the actuator adjusts the focal position of the optics with respect to the sample using the first filtered focus signal;
a second filter that filters the focus signal to produce a second filtered focus signal when a mean amplitude displacement between the first filtered focus signal and the focus signal is within a threshold range, wherein the second filter reduces the amplitude of noise in the focus signal more than the first filter, wherein the actuator adjusts the focal position of the optics with respect to the sample using the second filtered focus signal to focus the radiation on the sample.

30. The optical metrology device of claim 29, wherein the first filter comprises a Kalman filter with first filter parameters and the second filter comprises the Kalman filter with second filter parameters.

31. The optical metrology device of claim 29, wherein the focusing system further comprises:
a third filter that filters the focus signal to produce a third filtered focus signal, wherein the first filter reduces the amplitude of noise in the focus signal more than the third filter;
a comparator that receives the first filtered focus signal and the third filtered focus signal and produces an absolute value of a difference between the first filtered focus signal and the third filtered focus signal; and
a range filter that receives the absolute value of the difference and determines when the mean amplitude displacement within the threshold range.

32. The optical metrology device of claim 29, further comprising:
a switch coupled to the focusing system and the actuator, wherein the switch enables or disables the actuator from adjusting the focal position of the optics with respect to the sample;
wherein the focusing system further comprises:
a third filter that filters the focus signal to produce a third filtered focus signal, wherein the second filter reduces the amplitude of noise in the focus signal more than the third filter;
a comparator that receives the second filtered focus signal and the third filtered focus signal and produces an absolute value of a difference between the second filtered focus signal and the third filtered focus signal; and
a range filter that receives the absolute value of the difference and determines when a mean amplitude displacement between the second filtered focus signal and the third filtered focus signal is within a second threshold range, the range filter is coupled to the switch and causes the switch to disable the actuator from adjusting the focal position of the optics with respect to the sample when the mean amplitude displacement between the second filtered focus signal and the third filtered focus signal is within the second threshold range.

33. The optical metrology device of claim 29, wherein the actuator for adjusting the focal position of the optics with respect to the sample is a first actuator, the optical metrology device further comprising:
a second actuator for producing relative lateral movement between the optics and the sample to position the optics at a desired measurement location with respect to the sample;
wherein the first actuator adjusts the focal position of the optics with respect to the sample using the first filtered focus signal only after the second actuator has positioned the optics at the desired measurement location with respect to the sample.

34. The optical metrology device of claim 29, wherein the actuator for adjusting the focal position of the optics with respect to the sample is a first actuator, the optical metrology device further comprising:

a second actuator for producing relative lateral movement between the optics and the sample to position the optics at a desired measurement location with respect to the sample;

wherein the first actuator adjusts the focal position of the optics with respect to the sample using the first filtered focus signal while the second actuator produces the relative lateral movement between the optics and the sample;

wherein the first actuator adjusts the focal position of the optics with respect to the sample using the second filtered focus signal only after the second actuator has positioned the optics at the desired measurement location with respect to the sample.

35. The optical metrology device of claim 29, wherein the optical metrology device is an ellipsometer.

36. The optical metrology device of claim 35, further comprising:

a rotating optic that produces periodic noise in the focus signal;

wherein the first filter and the second filter the periodic noise in the focus signal.

* * * * *